(12) United States Patent
Gilat et al.

(10) Patent No.: US 7,491,312 B2
(45) Date of Patent: Feb. 17, 2009

(54) IDENTIFYING THERAPEUTIC COMPOUNDS BASED ON THEIR PHYSICAL-CHEMICAL PROPERTIES

(75) Inventors: Sylvain Gilat, San Francisco, CA (US); Gary Binyamin, Palo Alto, CA (US); Guy Miller, San Jose, CA (US)

(73) Assignee: Edison Pharmaceuticals, Inc., San Jose, CA (US)

(*) Notice: Subject to any disclaimer, the term of this patent is extended or adjusted under 35 U.S.C. 154(b) by 611 days.

(21) Appl. No.: 10/696,752

(22) Filed: Oct. 29, 2003

(65) Prior Publication Data

US 2004/0105817 A1  Jun. 3, 2004

Related U.S. Application Data

(60) Provisional application No. 60/487,734, filed on Jul. 16, 2003, provisional application No. 60/422,727, filed on Oct. 30, 2002.

(51) Int. Cl.
*G01N 27/26* (2006.01)

(52) U.S. Cl. .............................. 205/787; 435/4; 424/9.2

(58) Field of Classification Search ................ 205/775, 205/787; 204/403.01; 424/9.2; 435/4
See application file for complete search history.

(56) References Cited

U.S. PATENT DOCUMENTS

| | | | |
|---|---|---|---|
| 4,997,526 A | 3/1991 | Robblee | |
| 5,574,656 A | 11/1996 | Agrafiotis et al. | |
| 5,684,711 A | 11/1997 | Agrafiotis et al. | |
| 5,763,479 A | 6/1998 | Chayen et al. | |
| 5,874,461 A | 2/1999 | deChaffoy deCourcell | |
| 5,901,069 A | 5/1999 | Agrafiotis et al. | |
| 6,031,076 A | 2/2000 | Falb et al. | |
| 6,121,234 A | 9/2000 | Benet et al. | |
| 6,306,595 B1 | 10/2001 | Hendry | |
| 6,344,330 B1 | 2/2002 | Ellman et al. | |
| 6,372,772 B1 | 4/2002 | Kirkpatrick et al. | |
| 6,387,945 B2 | 5/2002 | Packer et al. | |
| 6,421,612 B1 | 7/2002 | Agrafiotis et al. | |
| 6,434,490 B1 | 8/2002 | Agrafiotis et al. | |
| 2002/0034537 A1 | 3/2002 | Schulze et al. | |
| 2002/0123069 A1 | 9/2002 | Johnson | |

(Continued)

FOREIGN PATENT DOCUMENTS

WO    WO-02/47680 A2    6/2002

(Continued)

OTHER PUBLICATIONS

Yang et al. (2001) "Estimation of the antioxidant activities of flavonoids from their oxidation potentials", Analytical Sciences 17(5):599-604.

(Continued)

*Primary Examiner*—Kaj K Olsen
(74) *Attorney, Agent, or Firm*—Morrison & Foerster LLP

(57) ABSTRACT

The present invention is directed to rapid and efficient methods of identifying therapeutic compounds by allowing only the most favorable molecules initially selected based on their physical-chemical profile falling within a range predefined by the physical-chemical/biological relationship of a previously tested small subset of compounds of same core structure to be assayed; and to the therapeutic compositions identified by said methods.

30 Claims, 7 Drawing Sheets

U.S. PATENT DOCUMENTS

2003/0014191 A1     1/2003    Agrafiotis et al.
2003/0033088 A1     2/2003    Agrafiotis et al.

FOREIGN PATENT DOCUMENTS

WO      WO-02/47680 A3    6/2002
WO      WO-02/053152 A1    7/2002

OTHER PUBLICATIONS

Bensasson et al. (1999) "Redox regulation of tumor cell toxicity by flavones from Lethedon tannaensis". Free Radical Biology & Medicine, 27(½):95-99.
Mouithys-Mickalad et al. (2001) "Electrooxidation potential as a tool in the early screening for new safer Clozapine-like analogues". J. Med. Chem, 44:769-776.
Cheng et al. (2002) "Phenolic antioxidants: electrochemical behavior and the mechanistic elements underlying their anodic oxidation reaction". Redox Report 7(6):395-402.
Aguilar-Martinez M. et al, J.Org. Chem. 1999, 64: 3684-3694.
Ashnagar A. et al., Biochim Biophys Acta 1984, 801(3): 351-9.
Ames Jr. et al., Epilepsia 1992, 33(5): 936-943.
Chevion S. et al., Free Radical Biology & Medicine 2000, 28(6):860-870.
Cos P. et al., J. Nat. Prod., 1998, 61: 71-76.
Crawford PW. et al., J. Electrochem. Soc. 1997, 144 (11): 3710-3715.
Crawford PW. et al., Bioelectrochemistry and Bioenergetics, 1986, 16:407-426.
Crawford PW. et al., Chem. Biol. Interactions, 1986, 60:67-84.
Ghose A. et al., J. Comb. Chem., 1999, 1, 55-68.
Hodnett EM. et al., J. Med. Chem. 1983, 26(40:570-4.
Hodnick WF et al., Biochem Pharmacol 1988, 37(13): 2607-11.
Kilmartin PA, Antioxidants & Redox Signaling 2001, 3(6): 941-955.
Kovacic P., Pharmaceutical Research, 1990, 7(3): 283-288.
Kovacic P., Free Rad. Res. Comms. 1990, 10(3): 185-192.
Kovacic P., Free Radical Biology and Medicine 1989, 6: 131-139.
Kunz KR, J. Med. Chem. 1991, 34(7):2281-6.
Lashuel, HA et al., J. Biol. Chem. 2002, 277(45):412881-42890.
Sakuma K et al., Arch Pharm Res. 1999 22(4):335-339.
Lipinski CA et al., Advanced Drug Delivery Reviews 1997, 23:3-25.
Pan SS. et al., Mol Pharmacol 1990, 37(6):966-70.
Rapta P. et al., Free Radic. Biol. Med. 1995, 18(5): 901-8.
Van Acker S. et al., Free Radic. Biol. Med. 1996, 20(3): 331-342.
Wardman P., Free Rad. Res. Comms. 1990, 8 (4-6): 219-229.
Livertoux, The superoxide production mediated by the redox cycling of xenobiotics in rat brain microsomes is dependent on their reduction . . . Brain research, 725, 207-216 (1996).
Hendrickson, Relationship of flavonoid oxidation potential and effect on rat hepatic microsomal metabolism of benzene . . . J. Pharm. & Biomed. Anlysis, 12,(3), 335-341 (1994).
Supplementary European Search Report issued on Jul. 9, 2008, for EP Patent Application No. 03 78 1483, filed on Oct. 29, 2003, 5 pages.

IDENTIFYING THERAPEUTIC COMPOUNDS BASED ON THEIR PHYSICAL-CHEMICAL PROPERTIES

CROSS-REFERENCE TO RELATED APPLICATIONS

This application claims priority under 35 U.S.C. 119(e) to provisional applications U.S. Ser. No. 60/422,727 filed on Oct. 30, 2002, and U.S. Ser. No. 60/487,734 filed on Jul. 16, 2003, incorporated herein by reference in its entirety.

FIELD OF INVENTION

The present invention is directed to novel methods for identifying therapeutic compounds based on their structural and physical-chemical properties, and to the therapeutic compositions identified by said methods.

BACKGROUND OF THE INVENTION

In response to the ever increasing demand for novel compounds useful in the effective treatment of various disorders, a variety of strategies for discovering and optimizing new therapeutics has been developed. For the most part these strategies are dependent upon techniques that allow identification of molecules binding to a given biological target.

In one such strategy, novel drugs are identified by screening compound libraries and determining which compounds have the highest therapeutic properties, and optimizing such properties by synthesizing structurally related analogs. The limitation of such an approach is that it is possible to synthesize and test only a very small subset of all possible molecules thereby resulting in a high probability that the most efficacious molecules will be missed.

In another approach novel drugs are identified by determining structure activity relationships (SAR) correlating a common structural feature of the molecule to target based biological activity. While widely used this method does not always yield active analogs indicating SAR alone may not be sufficient to warrant biological activity in all cases.

SAR activity by NMR as described in U.S. Pat. No. 5,698,401, relates to a process for identifying compounds which bind to a specific target molecule. In this approach the physical structure of a target protein is determined by nuclear magnetic resonance analysis (NMR) and the small molecule building blocks are identified that bind to the protein at nearby points on the protein surface. Adjacently binding small molecules are then coupled together with a linker in order to obtain compounds that bind to the target protein with higher affinity that the unlinked compounds alone. Thus, by having available the NMR structure of the target protein, the lengths of linkers for coupling two adjacently binding molecules can be determined and small molecules can be rationally designed. Although these methods are powerful they have serious limitations, such as the required amounts of target protein and the fact that the protein must be $^{15}$N-labeled to be useful for NMR studies.

With the advent of combinatorial chemistry and high throughput screening, numerous high-profile reviews have appeared in the literature that classify and prioritize the chemical space for drug discovery. Lipinski et al., *Adv. Drug. Deliv. Rev.*, 3-25, 1997, is a widely cited review that correlates physical-chemical properties of permeability and absorption with biological activity. This review defines the "rule of 5" which a molecule should generally not violate to be granted the status of "drug-like" molecule. The "rule of 5" states that poor absorption or permeation are more likely when there are more than 5-H bond donors (expressed as the sum of OHs and NHs); more than 10 H-bond acceptors (expressed as the sum of Ns and Os); the molecular weight is over 500; and the log P is greater than 5.

Ghose et al., *J. Comb. Chem.*, 1, 55-68, 1999, provides an analysis of some computable physical-chemical properties and chemical constitutions of known drug molecules available in the comprehensive Medicinal Chemistry (CMC) database and seven known drug classes. Their study showed qualifying ranges for calculated log P, refractivity, molecular weight, and total number of atoms.

In recent years, electronically active molecules, such as antioxidants and reductants, have been recognized as functioning in redox regulation of key biological processes such as immune response, cell-cell adhesion (e.g. atherosclerosis), cell proliferation, inflammation, metabolism, glucose uptake (diabetes), and programmed cell death (apoptosis).

It has been described in the art, that biological activity of certain compounds is related to their capacity to accept one or two electrons to form the corresponding radical anion or dianion, and that the electron-accepting capacity of these substances can be modified by directly adding substituents to the core structure. For these types of compounds, the attracting or donor effects of the substituents are very important in affecting the redox properties of the core structure system, either facilitating or interfering with the electron transfer, (see for example a study of the substituent effect on the redox properties of the quinone moiety, Aguilar-Martinez et al., *J. Org. Chem.*, 64, 3684-3694, 1999). If a molecule's core structure is affected by its substituents, a change of its voltammogram may occur representing a change in electron transfer (redox) properties.

The redox behavior of a series of structurally related flavonoids under physiological conditions has been investigated by Hodnik, W. F. et al, *Biochem. Pharmacol.*, 37 (13), 2607-11, 1988, as well as the relationship of flavonoids oxidation potential and effect on the hepatic metabolism, see Hendrickson, H. P. et al., *J. Pharm. Biomed. Anal.*, 12(3), 335-41, 1994. Half peak oxidation of flavonoids was measured and correlated to LPO inhibition data in Saskia et al., *Free Radic. Biol. Med.*, 20 (3), 331-342, 1996, and the redox intermediates of flavonoids and caffeic acid esters from propolis were studied by cyclic voltammetry, see Rapta, P. et al., *Free Radic. Biol. Med.*, 18(5), 901-8, 1995.

Structural activity relationship studies on apomorphine and its derivatives have been described by Lashuel, H. A. et al., *Journal of Biol. Chem.*, 45, 42881-42890, 2002, hereby incorporated by reference in its entirety.

Ashnagar A. et al., *Biochim. Biophys. Acta*, 801, 351-9, 1984, have described the measurements of reduction potentials of hydroxy-1,4-naphthoquinones and hydroxy-9,10-anthraquinones as well as the corresponding methoxy- and acetoxyquinones, and the role of internal hydrogen bonding and its bearing on the redox chemistry of the anthracycline antitumor quinones. The correlation among antitumor activity, quinone reduction potential and the logarithm of the partition coefficient (log P) was obtained by Kuntz et al., *J. Med. Chem.*, 34, 2281-6, 1991. The relationships of reductive potential, kinetics of enzymatic reduction, augmented oxygen consumption and cytotoxicity were determined for seven clinically relevant mitomycin antibiotics by Pan S. S. et al., *Mol. Pharmacol.*, 37, 966-70, 1997. Twelve 1,4-naphthoquinones were tested against the ascetic form of sarcoma and it was shown by statistical analysis that the most important molecular parameters determining their effectiveness in prolonging the life of mice bearing this tumor were their redox potentials, see Hodnett E. M. et al. *J. Med. Chem.*, 26, 570-4, 1983. Electrochemical properties of some biologically active quinone derivatives, furanquinones, pyridoquinones and diplamine, a cytotoxic pyridoacridine alkaloid, have been reported in Crawford, P. W. et al., *J. Electrochem. Soc.*, 144, 3710-3715, 1997, indicating a possible relationship between reduction potential and anticancer activity.

Cyclic voltammetry has been used for the detection of compounds in different solutions, see for example, Kilmartin, P. *Antioxidants and Redox Signaling*, 3, (6), 941-955, 2001, and in a redox control and monitoring high throughput screening platform used in conjunction with another detector, (see U.S. Application 2002/0123069), but heretofore cyclic voltammetry has not been used for the a priori identification of possible therapeutic candidates.

It is evident that there is a need for novel techniques useful for rapidly and efficiently identifying molecule compounds that are capable of having a therapeutic effect.

It has been surprisingly found that novel therapeutic molecules can be identified by their physical-chemical properties comprising a least one redox parameter and falling within a range predefined by the physical-chemical/biological relationship of a previously tested small subset of compounds with the same core structure.

SUMMARY OF THE INVENTION

The present invention relates to a rapid and efficient method of identifying therapeutic compounds, by allowing only the most favorable molecules initially selected based on their core structure and their physical-chemical characteristics to be further assayed.

The present invention relates to a method of identifying molecules with a specific core structure selectively targeting certain disorders, based on their physical-chemical profile falling within a range predefined by the physical-chemical/biological relationship of a previously tested subset of compounds. In the present invention, members of a small subset of compounds with a specific core structure are tested for particular physical-chemical characteristics comprising their redox profile, and for their biological activity, a relationship between the two parameters is established, and other potential drug candidates are screened based on their physical measurements falling within a range predefined by said physical-chemical biological relationship. If the physical-chemical profile is within the range defined by the relationship of physical-chemical and biological activity of the previously tested subset of compounds, they are subject to be considered therapeutic candidates. The physical property measurements may show better repeatability, reproducibility and lower variability over time than biological assays, and, since they do not involve living organisms, they may be less time-consuming and expensive.

In the present invention we describe a method of identifying therapeutic molecules that have both structural and electrochemical attributes that are critical determinants of their therapeutic benefit for redox-based metabolic disorders, such as ischemic, neurodegenerative and/or inflammation disorders, without the need for screening with biological assays all possible compounds and combinations thereof as is required in standard combinatorial library or SAR approaches.

The present invention is illustrated with molecules having scaffolds with stilbene, flavonoid, apomorphine, chroman, or quinone core structures to more clearly understand and practice the present invention. They should not be limiting the scope of the invention, but merely being representative thereof. The present invention also relates to the compositions comprising core structures identified by said methods.

In one embodiment, the invention relates to a rapid and efficient method of identifying and selecting therapeutic compounds with a predetermined core structure, said method comprising:
  establishing a relationship between physical-chemical profile and biological activity; said physical-chemical profile comprising one or more parameters selected from onset of oxidation, potential of oxidation, potential of reduction, reversibility of oxidation, reversibility of reduction, current of oxidation or current of reduction; and said biological activity being measured in an assay effective in detecting compounds for the treatment of a targeted disorder, preferably in a a cell-based assay;
  testing further potential therapeutic candidates with said core structure for their physical-chemical properties; and
  selecting therapeutic compounds based on their physical-chemical parameters falling within a range predefined by the physical-chemical/biological relationship of the previously tested subset of compounds.

In a particular embodiment, the molecules are selected if their parameter for onset of oxidation falls within the predefined range. In another particular embodiment the molecules are selected if their parameter for potential of first oxidation wave falls within the predefined range. In another particular embodiment, the molecules are selected if their parameter for reversibility of one or more oxidation waves fall within the predefined range. In another particular embodiment, the molecules are selected if their parameter for reversibility of one or more reduction waves fall within the predefined range. In another particular embodiment, the molecules are selected if their parameter for potential of first reduction wave falls within the predefined range.

In certain embodiments, the molecules are initially screened and selected based on their physical-chemical profile additionally comprising one or more parameters selected from energy profile parameters and transport profile parameters.

In another embodiment, the invention relates to a rapid and efficient method of identifying and selecting therapeutic molecules by using a population of organic molecules initially selected based on their physical-chemical profile, wherein said physical-chemical profile comprises a cyclic voltammetric profile.

In another embodiment, the invention relates to a therapeutic composition comprising a compound and/or a therapeutically acceptable excipient, selected by the method wherein
  a relationship is established between physical-chemical profile and biological activity, said physical-chemical profile comprising one or more parameters selected from onset of oxidation, potential of oxidation, potential of reduction, reversibility of oxidation, reversibility of reduction, current of oxidation or current of reduction; and said biological activity being measured in an assay effective in detecting compounds for the treatment of a targeted disorder, preferably in a a cell-based assay;
  further potential therapeutic candidates with said core structure are tested for their physical-chemical properties; and
  the therapeutic compounds are selected based on their physical-chemical parameters falling within a range predefined by the physical-chemical/biological relationship of the previously tested subset of compounds.

In another embodiment, the physical-chemical profile of a compound comprising a stilbene core is defined within the range predefined by the relationship between the physical-chemical profile comprising one or more parameters selected from potential of first oxidation or reduction waves, reversibility of said oxidation or reduction waves, and current of said oxidation or reduction waves; and the biological activity measuring the ability of the compound to protect energetically competent cells with a potency and efficacy in at least about 20%, preferably at least about 30%, of the cells tested in a cellular assay in a previously tested subset of compounds, and in another embodiment the cellular assay is selected from the High Glutamate-induced Oxidative Stress assay and the E-selectin (ELAM) assay.

In another embodiment, the invention relates to a method of identifying and selecting a therapeutic compound with a stilbene core structure for treating a condition characterized by oxidative stress, such as but not limited to inflammation, neurodegeneration, or ischemia; based on its physical-chemical profile comprising a parameter for potential of the first oxidation wave falling between about 800 mV and 1400 mV, and/or a parameter for reversibility of the first oxidation wave of about 20% or more.

In another embodiment the physical-chemical profile comprises a parameter for potential of the first oxidation wave that falls between about 800 mV and 1400 mV. In another embodiment the physical-chemical profile parameter comprises a parameter of reversibility of the first oxidation wave of 20% or more.

In another embodiment the invention relates to a method of identifying a therapeutic compound for treating a condition characterized by oxidative stress, such as but not limited to inflammation, neurodegeneration, or ischemia, comprising a redox active molecule comprising a core structure of Formula I:

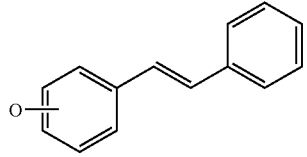

Formula I wherein additional substitution at the phenyl rings does not include a nitro group.

In another embodiment the physical-chemical profile of a compound of Formula I wherein additional substitution at the phenyl rings does not include a nitro group, is defined within the range predefined by the relationship between the physical-chemical profile comprising one or more parameters selected from potential of oxidation or reduction waves, reversibility of said oxidation or reduction waves, and current of said oxidation or reduction waves; and the biological activity measuring the ability of the compound to protect energetically competent cells with a potency and efficacy in at least about 20%, preferably at least about 30% of the cells tested in a previously tested subset of compounds, and in another embodiment the cellular assay is selected from the High Glutamate-induced Oxidative Stress assay and the E-selectin (ELAM) assay.

In another embodiment the invention relates to a method of identifying and selecting a therapeutic compound with a core structure of Formula I

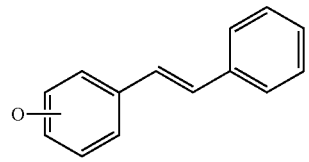

Formula I wherein additional substitution at the phenyl rings does not include a nitro group, for treating a condition characterized by oxidative stress, such as but not limited to inflammation, neurodegeneration, or ischemia; based on its physical-chemical profile comprising a parameter of potential of the first oxidation that falls below about 1000 mV.

In another embodiment the invention relates to a method of identifying a therapeutic compound for treating a condition characterized by oxidative stress, such as but not limited to inflammation, neurodegeneration, or ischemia comprising a redox active molecule comprising a core structure of Formula I:

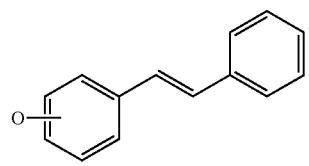

Formula I wherein additional substitution at the phenyl rings includes a nitro group.

In another embodiment the physical-chemical profile of a compound of Formula I wherein additional substitution at the phenyl rings includes a nitro group, is defined within the range predefined by the relationship between the physical-chemical profile comprising one or more parameters selected from potential of oxidation or reduction waves, reversibility of said oxidation or reduction waves, and current of said oxidation or reduction waves; and the biological activity measuring the ability of the compound to protect energetically competent cells with a potency and efficacy in at least about 20%, preferably at least about 30% of the cells tested in a previously tested subset of compounds, and in another embodiment the cellular assay is selected from the High Glutamate-induced Oxidative Stress assay and the E-selectin (ELAM) assay.

In another embodiment the invention relates to a method of identifying a therapeutic compound with a core structure of Formula I, wherein additional substitution at the phenyl rings includes a nitro group, for treating a condition characterized by oxidative stress, such as but not limited to inflammation, neurodegeneration, or ischemia based on the physical-chemical profile comprising:

a parameter for potential of first oxidation wave falling between about 950 mV and 1250 mV; and/or a parameter for reversibility of first oxidation wave falling that measures more than 20%.

In another embodiment the physical-chemical profile comprises a parameter for potential of the first oxidation wave that falls between about 950 mV and 1250 mV. In another embodiment the physical-chemical profile comprises a parameter for reversibility of the first oxidation wave that measures more than 20%.

In another embodiment, the invention relates to a therapeutic composition comprising a compound and/or a therapeutically acceptable excipient, wherein said compound is selected by the method described herein based on its stilbene core structure and its physical-chemical profile comprising:
 a parameter for potential of the first oxidation wave falling between about 800 mV and 1500 mV, and/or
 a parameter for reversibility of the first oxidation wave of about 20% or more.

In another embodiment the invention relates to a therapeutic composition comprising a compound and/or a therapeutically acceptable excipient, selected by the method as described herein, based on its core structure of Formula I

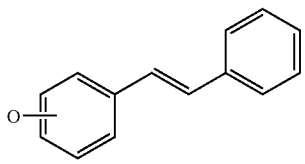

Formula I wherein additional substitution at the phenyl rings includes a nitro group;

and its physical-chemical profile comprising a parameter for potential of the first oxidation wave that falls below about 1000 mV.

In another embodiment the invention relates to a therapeutic composition comprising a compound and/or a therapeutically acceptable excipient; selected by the method as described herein based on its core structure of Formula I

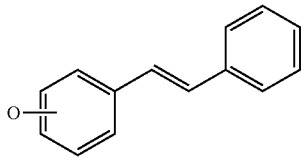

Formula I wherein additional substitution at the phenyl rings includes a nitro group;

and its physical-chemical profile comprising
 a parameter for potential of the first oxidation wave falling between about 950 mV and 1250 mV; and/or
 a parameter for reversibility of first oxidation wave measuring more than 20%.

In another embodiment the invention relates to a method of identifying a therapeutic compound for treating a condition characterized by oxidative stress comprising a redox active molecule with a flavonoid core structure, if its physical-chemical profile is defined within the range predefined by the relationship between the physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to reduce the expression of E-selectin (ELAM) at $EC_{50}$ in a range of less than about 30 μM, preferably less than about 20 μM. In another embodiment, the physical-chemical profile of a compound comprising a flavonoid core, is defined within the range predefined by the relationship between the physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to protect energetically competent cells with a potency and efficacy in at least about 30% of the cells tested in a High Glutamate-induced Oxidative Stress (HGOS) assay.

In another embodiment, the invention relates to a method of identifying and selecting a therapeutic compound with a flavonoid core structure for treating a condition characterized by oxidative stress, such as neurodegeneration or ischemia; based on the physical-chemical profile comprising a parameter for potential of the first oxidation wave that falls between about 1050 mV and 1450 mV.

In another embodiment, the invention relates to a therapeutic composition comprising a compound and/or a therapeutically acceptable excipient, selected by the method as described herein based on its flavonoid core structure and its physical-chemical profile comprising a parameter for potential of the first oxidation wave that falls between about 1050 mV and 1450 mV.

In another embodiment, the invention relates to a method of identifying and selecting a therapeutic compound with a flavonoid core structure of Formula II,

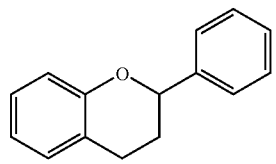

Formula II wherein one or more of the substituents are hydroxy groups, for treating a condition characterized by inflammation, based on the physical-chemical profile comprising one or more parameters selected from onset of oxidation, potential of oxidation or reduction waves, reversibility of said oxidation or reduction waves, and current of said oxidation or reduction waves; if it comprises a parameter for onset of oxidation that falls between about 850 mV and 1050 mV.

In another embodiment, the invention relates to a therapeutic composition comprising a compound and/or a therapeutically acceptable excipient, selected by the method as described herein based on its flavonoid core structure of Formula II wherein none of the substituents are hydroxy groups, and its physical-chemical profile comprising a parameter for potential of the onset of oxidation that falls between about 850 mV and 1050 mV.

In another embodiment, the invention relates to a method of identifying and selecting a therapeutic compound with a flavonoid core structure of Formula II,

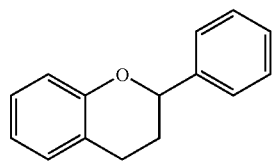

Formula II wherein one or more of the substituents are hydroxy groups, for treating a condition characterized by inflammation, based on the physical-chemical profile comprising one or more parameters selected from onset of oxidation, potential of oxidation or reduction waves, reversibility of said oxidation or reduction waves, and current of said oxidation or reduction waves; if it comprises a parameter for onset of oxidation that falls between about 350 mV and 650 mV.

In another embodiment, the invention relates to a therapeutic composition comprising a compound and/or a therapeutically acceptable excipient, selected by the method as described herein based on its flavonoid core structure of Formula II, wherein one or more of the substituents are hydroxy groups, and its physical-chemical profile comprising a parameter for potential of the first oxidation wave that falls between about 350 mV and 650 mV.

In another embodiment, the invention relates to a rapid and efficient method of identifying and selecting therapeutic compounds, said method comprising screening a small subset of compounds with an apomorphine core structure of Formula III,

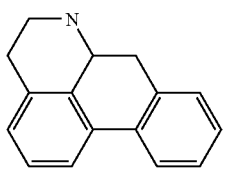

Formula III for their physical-chemical profile, comprising one or more parameters selected from onset of oxidation, potential of oxidation or reduction waves, reversibility of said oxidation or reduction waves, current of said oxidation or reduction waves; and for their biological activity in an assay of interest; establishing a relationship between physical-chemical profile and biological activity; screening further potential therapeutic candidates for their physical-chemical properties; and selecting the therapeutic molecules based on their physical-chemical properties falling within the range predefined by the physical-chemical/biological relationship of the previously tested subset of compounds.

In another embodiment the biological assay is a neurodegenerative assay, particularly the biological assay is the amyloid-β fibril formation assay able to detect molecules effective for the treatment of a progressive neurodegenerative disease characterized by the presence of extracellular amyloid plaques and intraneuronal neurofibrillary tangles in the brain such as in Alzheimer's disease. In another embodiment the assay is the Thioflavin T assay as described in Lashuel et al. see supra. In another embodiment the assay is the High Glutamate Oxidative Stress (HGOS) assay.

In another embodiment, the biological assay is an inflammation assay. In another embodiment the physical-chemical profile comprises the potential of oxidation wave. In another embodiment the physical-chemical profile comprises the potential of reduction wave.

In another embodiment, the physical-chemical profile of a compound comprising an apomorphine core, is defined within the range predefined by the relationship between the physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to reduce amyloid-β fibril formation based on quantitative Thioflavin T binding assay to less than about 30%. In another embodiment, the physical-chemical profile of a compound comprising an apomorphine core, is defined within the range predefined by the relationship between the physical-chemical profile and the biological activity measuring the ability of the compound to reduce inflammation in the ELAM at $EC_{50}$ in a range of less than about 50 μM, preferably of less than about 30 μM.

In another embodiment, the invention relates to a method of identifying and selecting a therapeutic compound with an apomorphine core structure for treating a neurodegenerative condition, particularly a condition characterized by inhibition of amyloid-β fibril formation, such as Alzheimer's; based on the physical-chemical profile comprising a parameter for potential of the first oxidation wave that falls under about 1250 mV.

In another embodiment, the invention relates to a method of identifying and selecting a therapeutic compound with an apomorphine core structure for treating a neurodegenerative condition, particularly a condition characterized by inhibition of amyloid-β fibril formation; based on the physical-chemical profile comprising a parameter for potential of the first reduction wave that is more negative than about −790 mV.

In another embodiment, the invention relates to a therapeutic composition for the treatment of a condition characterized by neurodegeneration, particularly by inhibition of amyloid-β fibril formation, comprising a compound and/or a therapeutically acceptable excipient, wherein said compound is selected by the method described herein based on its apomorphine core structure, and its physical-chemical profile comprising a parameter for potential of the first oxidation wave that falls under about 1250 mV and/or a parameter for potential of the first reduction wave that is more negative than about −790 mV.

In another embodiment, the invention relates to a rapid and efficient method of identifying and selecting therapeutic compounds, said method comprising screening a small subset of compounds with a quinone core structure for their physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to reduce the expression of E-selectin (ELAM) at $EC_{50}$ in a range of less than about 50 μM, preferably of less than about 30 μM, and selecting the therapeutic molecules based on their physical-chemical properties falling within the range predefined by the physical-chemical/biological relationship of the previously tested subset of compounds.

In another embodiment, the invention relates to a method of identifying and selecting a therapeutic compound with a quinone core structure for treating a condition characterized by oxidative stress; if it comprises a parameter for total reversibility of reduction of about 75% or more.

In another embodiment, the invention relates to a therapeutic composition for the treatment of oxidative stress comprising a compound and/or a therapeutically acceptable excipient, wherein said compound is selected by the method described herein, based on its quinone core, and its physical-chemical profile comprising a parameter for total reversibility of reduction of about 75% or more.

In certain embodiments of this invention the condition to be treated is inflammation. In other embodiments of this invention the condition to be treated is ischemia. In other embodiments of this invention the condition to be treated is a neurodegenerative condition. In certain embodiments the condition to be treated is Alzheimer's disease.

In another embodiment the invention relates to a method of identifying a therapeutic compound for treating a condition characterized by oxidative stress comprising a redox active molecule with a chroman core structure of Formula IV,

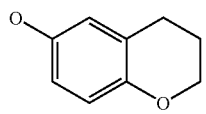

Formula IV if its physical-chemical profile is defined within the range predefined by the relationship between the physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to protect energetically competent cells with a potency and efficacy in at least about 20%, preferably at least about 30%, of the cells tested in a previously tested subset of compounds. In another embodiment, the physical-chemical profile of a compound comprising a chroman core structure of Formula IV, is defined within the range predefined by the relationship between the physical-chemical profile comprising one or more parameters selected from onset of oxidation, potential of oxidation or reduction waves, reversibility of said oxidation or reduction waves, and current of said oxidation or reduction waves; and the biological activity measuring the ability of the compound to protect energetically competent cells with a potency and efficacy in at least about 30% of the cells tested in a High Glutamate-induced Oxidative Stress (HGOS) assay.

In another embodiment, the invention relates to a method of identifying and selecting a therapeutic compound with a chroman core of Formula IV structure for treating a condition characterized by oxidative stress, such as neurodegeneration or ischemia; based on the physical-chemical profile comprising a parameter for potential of the first oxidation wave that falls between about 850 mV and 1200 mV.

In another embodiment, the invention relates to a therapeutic composition comprising a compound and/or a therapeutically acceptable excipient, selected by the method as described herein based on its chroman core structure of Formula IV and its physical-chemical profile comprising a parameter for potential of the first oxidation wave that falls between about 850 mV and 1200 mV.

The features, aspects and advantages of the present invention will become better understood with regard to the following description, claims, and accompanying drawings.

DETAILED DESCRIPTION OF THE INVENTION

Figure 1:
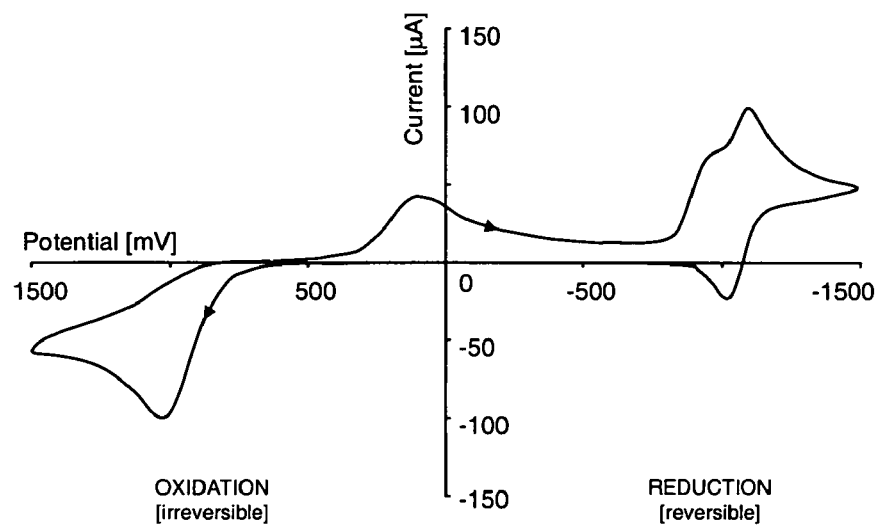
FIG. 1 illustrates a cyclic voltammogram of a stilbene analog showing potential of oxidation wave, reversibility of reduction wave and potential of reduction wave.
Figure 2:
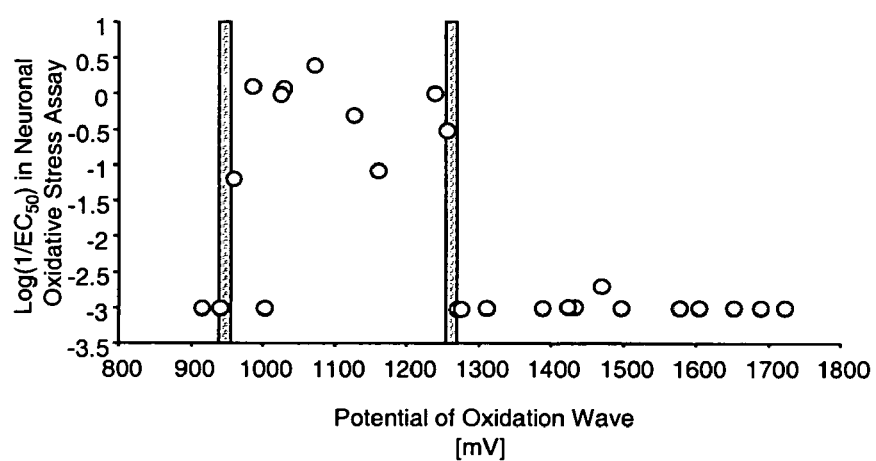
FIG. 2 illustrates the graph of oxidation potential plotted against activity in log ($1/EC_{50}$) in the neuronal oxidative stress assay (HGOS) of certain stilbene analogs, wherein one of the rings is further substituted with a nitro group. Certain compounds with a potential of the first oxidation wave ranging between 950 and 1250 mV show activity in the neuronal oxidative stress assay.
Figure 3:
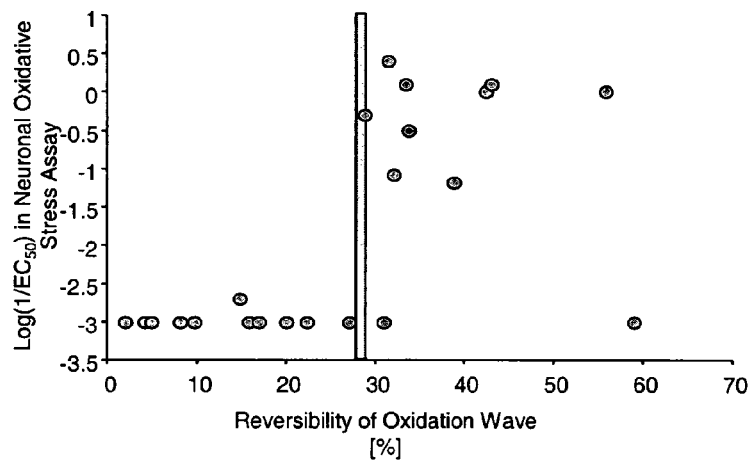
FIG. 3 illustrates the graph of % oxidative reversibility plotted against activity in log ($1/EC_{50}$) in the neuronal oxidative stress assay (HGOS) of certain stilbene analogs, wherein one of the rings is further substituted with a nitro group. Certain compounds with reversibility of the first oxidation wave of more than 20% show activity in the neuronal oxidative stress assay.
Figure 4:
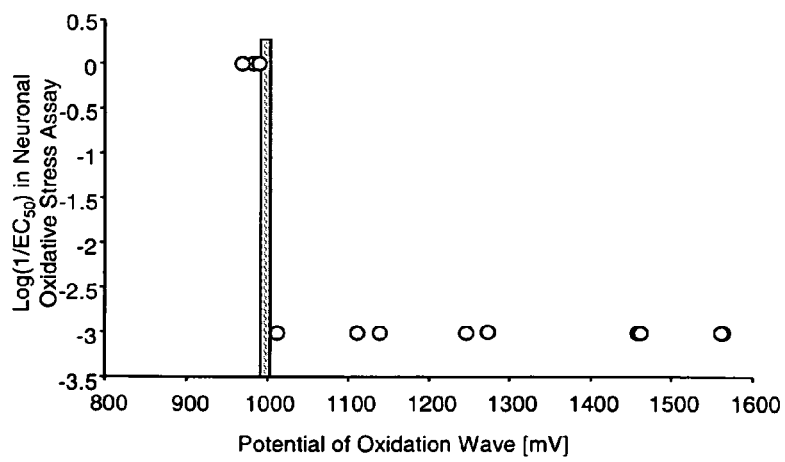
FIG. 4 illustrates the graph of oxidation potential plotted against activity in log ($1/EC_{50}$) in the neuronal oxidative stress assay (HGOS) of certain stilbene analogs, wherein none of the rings is further substituted with a nitro group. Certain compounds with a potential of the first oxidation wave ranging below 1000 mV show activity in the neuronal redox assay.
Figure 5:
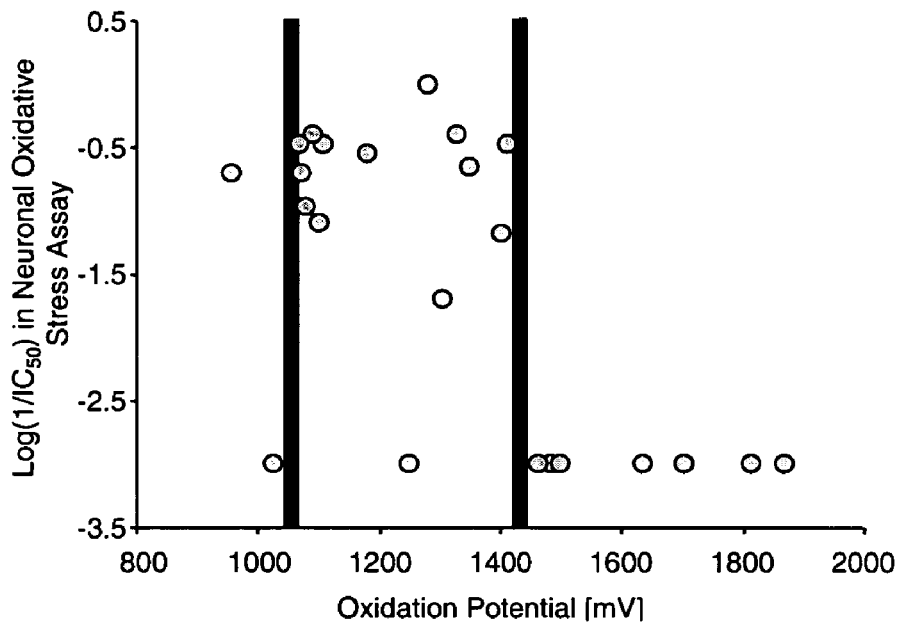
FIG. 5 illustrates the graph of oxidation potential plotted against activity in log ($1/EC_{50}$) in the neuronal oxidative stress assay (HGOS) of certain analogs with a flavonoid core structure.
Figure 6:
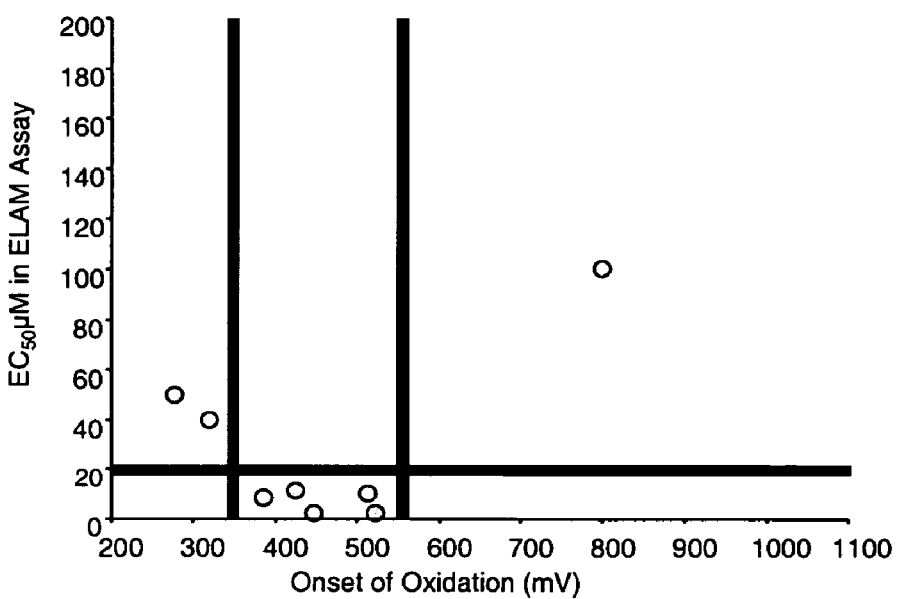
FIG. 6 illustrates the graph of onset oxidation plotted against activity in $EC_{50}$ in the ELAM assay of certain analogs with a flavonoid core structure wherein some of the substituents are hydroxy groups. Certain compounds with an onset of oxidation wave ranging between 350 mV and 650 mV show activity at $EC_{50}$ under 30 μM in the ELAM assay.
Figure 7:
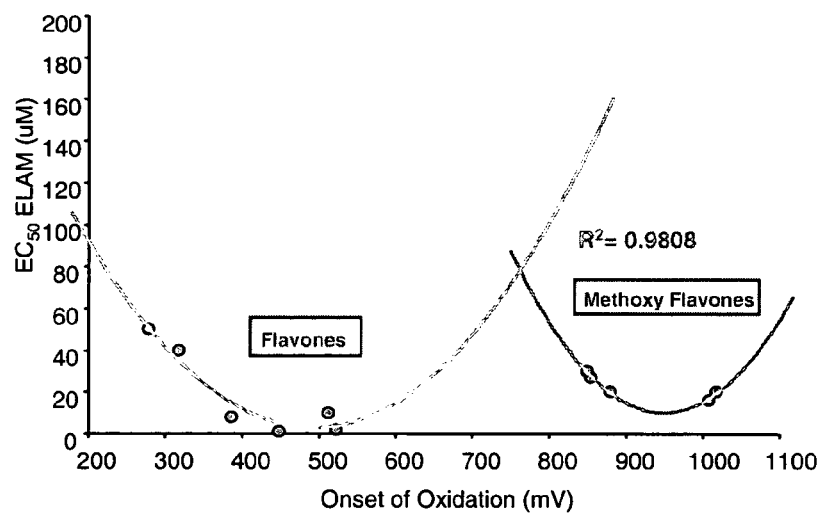
FIG. 7 illustrates the graph of onset oxidation plotted against activity in $EC_{50}$ in the ELAM assay of certain compounds with a flavonoid core structure. Active flavonoids compounds wherein some of the substituents are hydroxy groups fall within an onset of oxidation range between 350 mV and 650 mV, and compounds wherein none of the substituents are hydroxy groups fall within an onset of oxidation range between 850 mV and 1050 mV.
Figure 8:
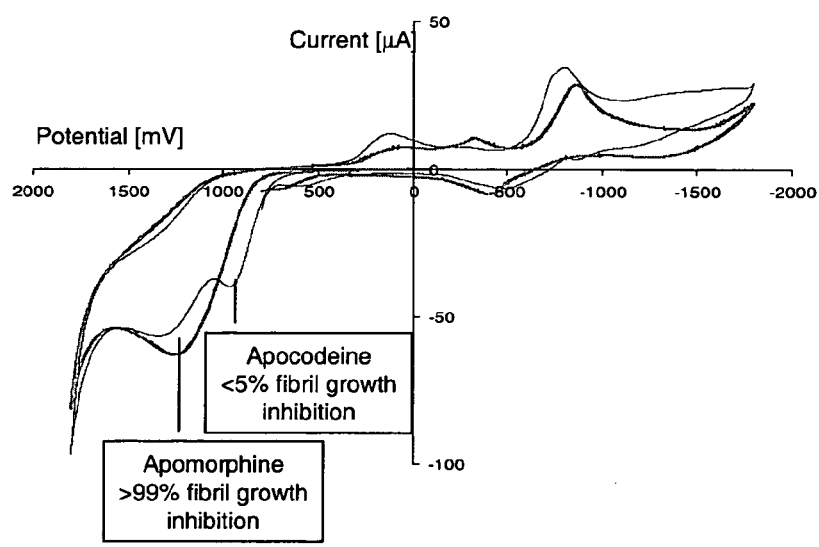
FIG. 8 illustrates the voltammograms of two compounds with an apomorphine core structure: apomorphine which reduces fibril growth by 99% and apocodeine which reduces the fibril growth by 5%. These voltammograms show that a minor variation in structure induces a variation in redox current.
Figure 9:
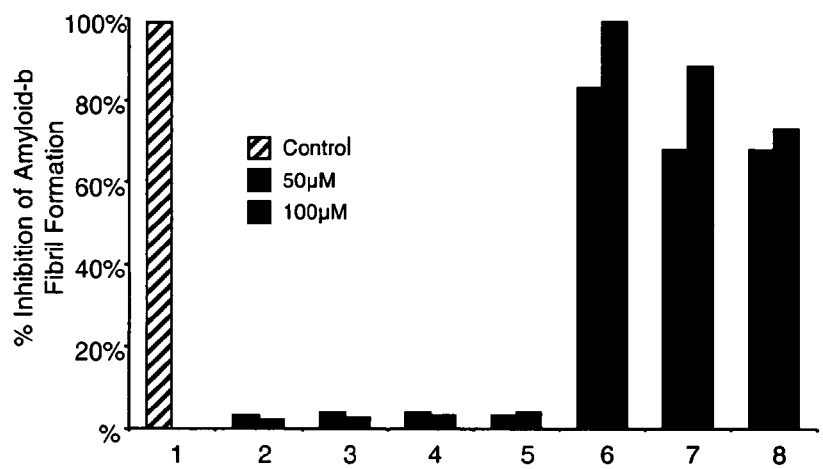
FIG. 9 illustrates the percent of fibril formation inhibition based on quantitative Thioflavin T binding assay in the presence of the six compounds with an apomorphine core structure: norapomorphine, 2,10,11-trihydroxyaporphine, propylnorapomorphine, apocodeine, isocorydine, and bulbocapnine as described in Lashuel, H. A. et al., *J. Bio. Chem,* 227 (45), 42881-42890, .,2002.
Figure 10:
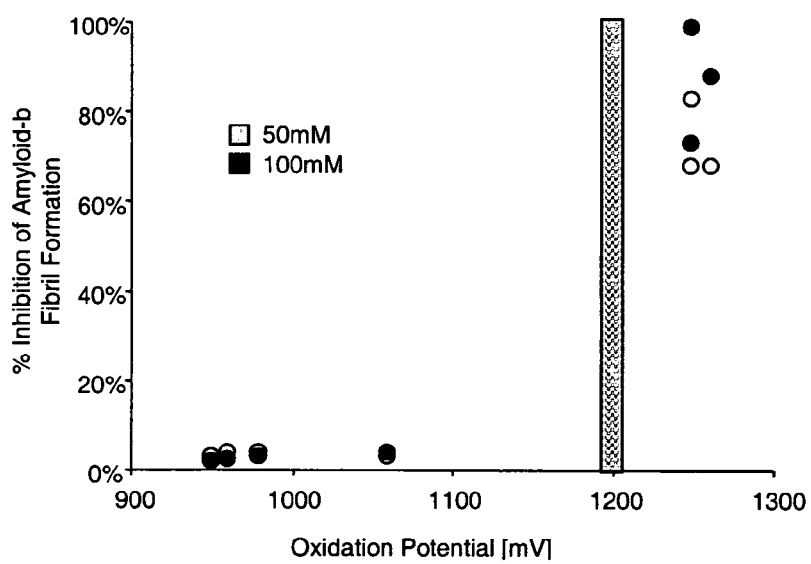
FIG. 10 illustrates the graph of percent of fibril formation at two different concentrations (50 mM and 100 mM) vs. potential of first oxidation wave of seven compounds with an apomorphine core structure. The compounds with a potential of first oxidation wave under 1250 mV show strong reduction of fibril formation in the Thioflavin T binding assay.
Figure 11:
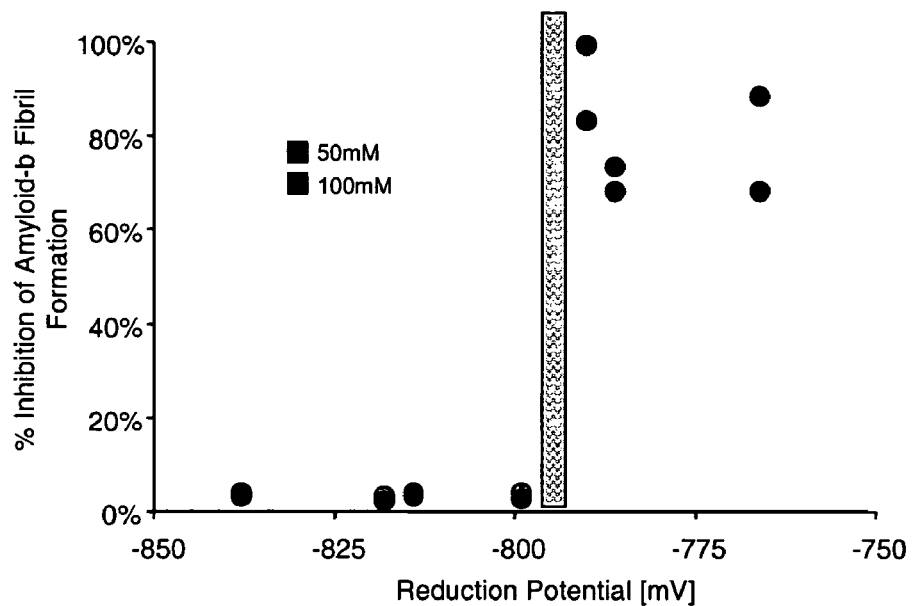
FIG. 11 illustrates the graph of percent of fibril formation at two different concentrations (50 mM and 100 mM) vs. potential of first reduction wave of six compounds with an apomorphine core structure. The compounds with a potential of first reduction wave more negative than −790 mV show strong reduction of fibril formation in the Thioflavin T binding assay.
Figure 12:
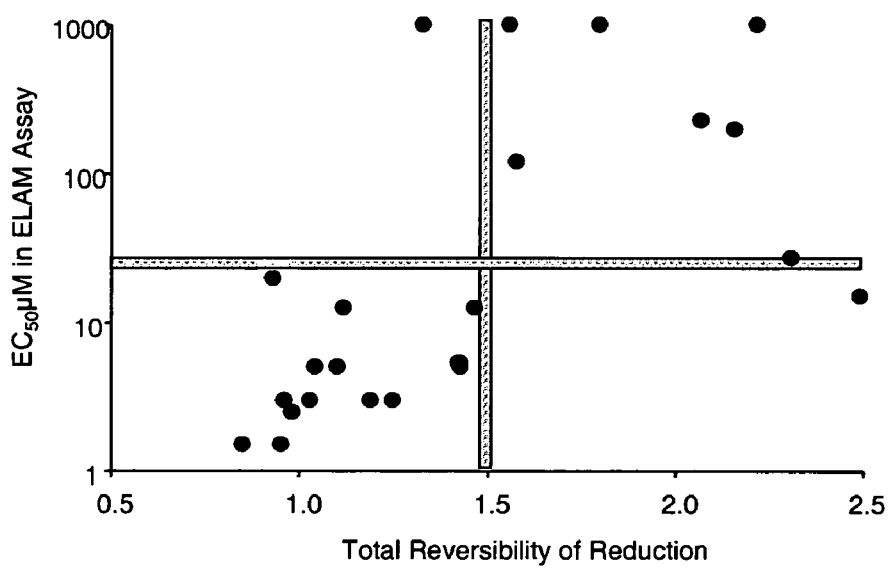
FIG. 12 illustrates the graph of reversibility of reduction waves vs. biological activity in the ELAM assay in $EC_{50}$ of compounds with a quinone core structure, wherein the total reversibility of reduction is the ratio of the current peak of reduction wave over the current peak of reoxidation waves or, in the case of more than one wave, the ratio of the mathematical addition of the current peaks of reduction waves over the mathematical addition of the current peaks of reoxidation waves.
Figure 13:
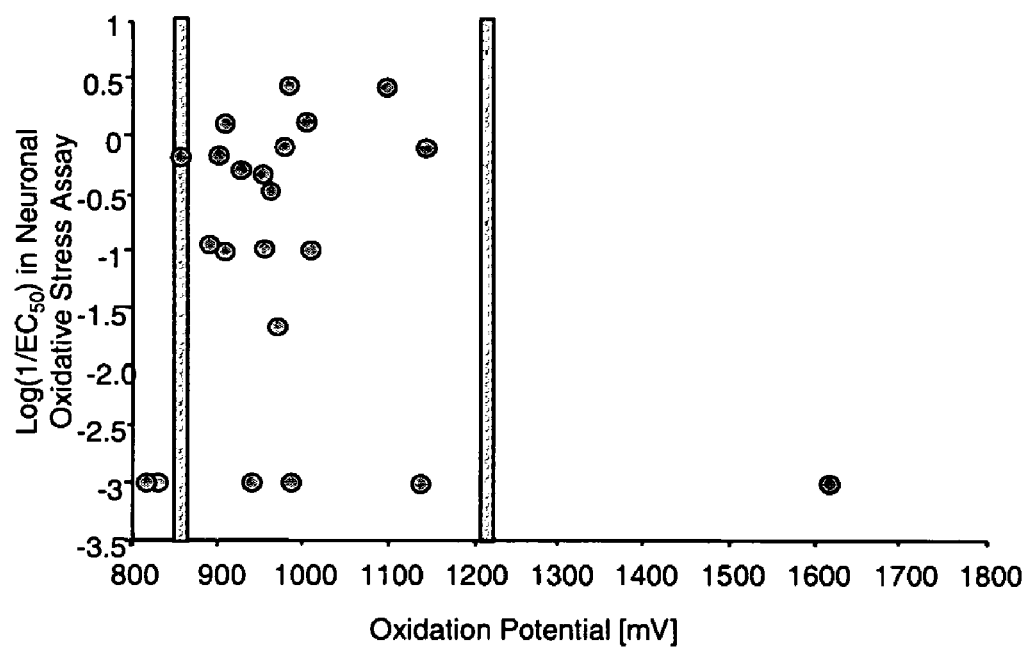
FIG. 13 illustrates the graph of oxidation potential plotted against activity in log ($1/EC_{50}$) in the neuronal oxidative stress assay (HGOS) of certain chromans. Certain compounds with a potential of the first oxidation wave ranging between 850 and 1200 mV show activity in the neuronal oxidative stress assay.

The interaction of a molecule with a biological target may not be limited to structural recognition alone. Other types of interaction may occur, and some of them may involve the exchange of one or more charges. Because of their distinct electronic distribution, molecules exhibit different physical-chemical profiles, particularly redox profiles, i.e. the measure of an ability to give or accept charges, the number of charges exchanged, the kinetics of the process, and the subsequent molecular mechanisms that follow the addition or subtraction of charges. Various electroanalytical techniques can be employed to determine the physical-chemical profile. Cyclic voltammetry is a technique that yields quantitative information on the above parameters. The redox profile of a molecule is well characterized by its cyclic voltammogram.

Other specific electroanalytical techniques may also be used to measure redox profile, such as for example single cyclic voltammetry, continuous cyclic voltammetry (with and without the integration of current), square wave voltammetry, square wave stripping voltammetry, AC voltammetry, choromoamperometry, chronocoulometry, chronopotentiometry, as well as various potentiostatic and galvanostatic techniques can be employed. A description of various electroanalytical techniques can be found in numerous textbooks, such as. Monk S, *Fundamentals of Electroanalytical Chemistry,* Wiley & Sons, New York, 156-175, 2001, or Bard A. J. et al, *Electrochemical Methods,* Wiley & Sons, New York, 1980, Ch. 6. The above stated electroanalytical techniques should not be considered as limiting the scope of the invention, but merely as being illustrative and representative thereof.

The redox properties of a molecule can be acquired from a variety of sources including cyclic voltammetry, in which the compound is characterized by the current-potential relationship exhibited at an electrode such as for example platinum, gold, or glassy carbon electrodes. In this technique the potential of a stationary electrode is changed linearly with time, starting from a fixed potential and moving to potentials more reductive or more oxidative. After traversing the potential region in which one or more electrode reactions take place, the direction of the linear sweep is reversed and the electrode reactions of intermediates and products that may have been formed during the forward scan can be detected. This has the advantage that the product of the electron transfer reaction that occurred in the previous scan can be probed again in the current scan. Cyclic voltammetry is a simple and direct method for measuring the formal potential of a half reaction when both oxidized and reduced forms are stable during the time required to obtain the current-potential curve. The resulting plot of current versus potential is termed a cyclic voltammogram. A cyclic voltammogram is a complicated, time-dependent function of a large number of physical and chemical parameters. It will give information on the anodic and cathodic peak potentials, the half-peak potential of the oxidation wave, the peak separation, the potential midway between the anodic and the cathodic peak. Only in the case where a redox system remains in equilibrium throughout the potential scan is the voltammogram reversible. The shape of a voltammogram can be significantly altered if there are coupled chemical reactions either before or after the electrochemical process. The mechanism, the rate, and the equilibrium constants of the process can all play a part in the final shape of the voltammogram that characterizes a certain molecule. Cyclic voltammetry is a powerful tool for the determination of formal redox potentials, detection of chemical reactions that precede or follow the electrochemical reaction, and evaluation of electron transfer kinetics.

A cyclic voltammogram yields data on the ability of the molecule to shed one or more electrons measured by the oxidation potential, the relative number of electrons exchanged measured by the oxidation current, the reversibility of the oxidation process measured by the ratio of the oxidation current to the corresponding reduction current, and the kinetics of the oxidized species measured through variation of the scan rate; as well as the ability of the molecule to accept one or more electrons measured by the reduction potential, the number of electrons exchanged measured by the reduction current, the reversibility of the reduction process measured by the ratio of the reduction current to the corresponding oxidation current; and the stability of the reduced species measured through variation of the scan rate.

Square wave voltammetry is a technique that yields quantitative information on the ability of the molecule to shed or accept one or more electrons with a very low detection limit due to its pulsed voltammetric technique. The primary advantage of the pulse voltammetric techniques is their ability to discriminate against charging current. As a result the pulse techniques are more sensitive to oxidation and reduction currents than conventional voltammetry. Square wave voltammetry yields peaks for faradic processes, where the peak height is directly proportional to the concentration of the species in solution. This results in improved resolution for multiple analyte systems and more convenient quantization. See for example, O'Cea, J. et al "Theory of Square Wave Voltammetry for Kinetic Systems", *Anal. Chem.* 53(4), 695, 1981 and Krause, J et al. "Analytical Application of Square Wave Voltammetry", *Anal. Chem.* 41(11),1365, 1969.

Even greater sensitivity when conducting measurements can be attained by using Stripping Square Wave Voltammetry, in which the species of interest is concentrated into the working electrode by electrochemical means before doing the analysis. With a sufficiently long concentration step, the concentration of the substance will be much higher in the electrode than in the sample solution. If the electrode potential is then scanned, the substance will be stripped from the electrode causing an increase in the cell current as this process occurs. The advantages of square wave stripping voltammetry over linear sweep are:

- it incorporates a pulsed waveform thus enhancing the sensitivity by repeated oxidation and reduction of the same analyte species;
- it is a purely subtractive technique, thus limiting currents due to dissolved species such as oxygen not interfere with the analytical signal;
- it is a fast technique and can be obtained in a matter of seconds;
- it provides kinetic information because of the ability to analyze both the forward and reverse currents as well as the net current, information about reaction reversibility, and electrode structure can be obtained easily.

In order to measure signals it is beneficial to utilize electrodes at which the competing redox reactions, such as, for example, the hydrogen evolution reaction or oxygen evolution reaction, do not interfere. This can be achieved by employing electrodes characterized by sufficiently high overpotential towards the competing reactions, such as but not limited to platinum, gold and glassy carbon. The working electrode may be stationary or rotating, of any geometry, and can include convective mixing. The measurements can be done in a variety of systems including but not limited to oxygenated or non-oxygenated environments, and protonated and non-protonated environments.

The electro-chemical measurement effected herein is typically conducted in a three-electrode system (working electrode/counter electrode/reference electrode) or, possibly a two electrode system (working electrode/counter electrode). The area of the counter electrode may typically be larger than that of the measuring electrode.

The redox profiles of the compounds of the present invention were measured by cyclic voltammetry, as described in Example 1 or by square wave voltammetry, as described in Example 2. All stated potential values are stated versus a silver/silver chloride reference electrode described in Examples 1 and 2. Those skilled in the art will appreciate that the silver/silver chloride electrode may be substituted with other reference electrodes, and that such substitution can result in different values, but this does not depart from the true spirit and scope of the invention.

The physical-chemical profile of this invention comprises a redox profile and its related physical measurements, optionally in conjunction with an energy profile and/or a transport profile and their related physical measurements.

The energy profile of a molecule can be acquired from its optical values such as linear emission, linear absorption and non-linear absorption. Linear emission is measured by the wavelength of maximum fluorescence $\lambda_{em}$, i.e. the radiating energy released by the stabilization of an electron from a high energy level (LUMO) to a lower energy level (HOMO); and/or by quantum yield of fluorescence $\Phi$, i.e. the probability of the molecule to stabilize an electron from its high energy level (LUMO) to a lower energy level (HOMO). Linear absorption is measured by the wavelength of maximum absorption $\lambda_{max}$, i.e. the amount of energy needed to eject an electron from the main energy level of the molecule to the next higher energy level with the highest probability; and/or molar extinction coefficient $\epsilon$, i.e. the probability of the molecule to eject an electron from its main energy level to next higher energy level when it receives the proper amount of energy; and/or the longest wavelength of absorption $\lambda_{end}$, i.e. the minimum energy needed to eject an electron form the main energy level of the molecule. Polarizability $\Delta\lambda_{pol}$ is measured by the ability of the electron cloud of the molecule to be shaped by an external electromagnetic field. Polarizability measurements are conducted by solvatochromism, measuring the shift in wavelength of maximum absorption as a function of solvent polarity (e.g. between octanol and DMSO).

The transport profile of a molecule can be acquired from its partition coefficient, and/or diffusion constant, and/or molecular weight, and/or melting point.

In order to establish a relationship between physical-chemical profile and biological activity of a small subset of molecules, all the quantitative physical parameters of such molecules are plotted versus a particular biological assay value, and for a well defined population correlations may emerge if any of the physical parameters is related to a biological activity. The plotting may be done manually or with the help of computer programs well known in the art such as Microsoft Excel®.

The biological activity of the small subset of compounds can be assessed by any assay deemed relevant to the target of interest. In the present invention the biological activity of some of these compounds was determined using an in vitro model well recognized in the art for determining the degree of dysfunction of the cells when exposed to stress. In vitro models of ischemia approximate oxygen and glucose deprivation that mimic in vivo conditions, for example, by placing neuronal cultures into large anaerobic of hypoxic chambers and exchanging culture medium with de-oxygenated and defined ionic composition media. The toxic overstimulation of neuronal glutamate receptors, especially N-methyl-D-aspartate (NMDA) receptors contribute to hypoxic-ischemic neuronal injury (Choi, D. M., *Neuron,* 1: 623-634, 1988), ischemic induction of reactive oxygen species (ROS) (Watson, B. D. et al., Ann NY Acad Sci., 59: 269-281, 1988), excessive calcium influx (Grotta, J. C., *Stroke,* 19: 447-454, 1988), arachidonic acid increase (Siesjo, B. K., *J. Cereb. Blood Flow Metab.,* 1: 155-186, 1981) and DNA damage (MacManus, J. P. et al., *Neurosci. Lett.,* 164: 89-92, 1993), each causing a cascade of neurodegeneration.

Oxidative stress has emerged as one of the major factors in the neurodegenerative disease and may contribute to neuronal damage from ischemia (see e.g., Coyle J. T. et al., *Science* 262, 689-695, 1993; or Beal M. F, *Curr. Opin. Neurobiol.;* 6, 661-666, 1996). Reactive oxygen species (ROS), which are generated as by-products of many metabolic processes including the mitochondrial electron transport chain, (Tan S. et al., *J. Cell Biol.* 141, 1423-1432, 1998), monoamine metabolism (Maher P. et al., *J. Neurosci.* 16, 6394-6401, 1996), and arachidonic acid oxidation (Li Y., et al., *Neuron* 19, 453-463, 1997) may be the principal mediators for cell death in oxidatively stressed neuronal cells (Chan P. H., Role of oxidants in ischemic brain damage; *Stroke* 27, 1124-1129, 1996 and Hosler B. A. et al.; *Curr. Opin. Neurol.* 9, 486-491. 1996). The damage on cellular organelles and macromolecules by chemical reactions with ROS can initiate an apoptotic program of cell death (Hosler B. A. et al., see supra) or lead to neurosis (Choi D. W. *Curr. Opin. Neurobiol.* 8, 667-672, 1996).

Mouse dopaminergic neuronal cell lines are useful for examining high glutamate-induced oxidative stress (HGOS). The cytotoxic effect of glutamate is not due to excitotoxicity, as this cell line is devoid of inotropic glutamate receptors. Rather, the glutamate-induced toxicity of dopaminergic cells is associated with an inhibition of cystine transport (Murphy T. H., et al., *Neuron* 2, 1547-1558, 1989), which subsequently leads to depletion of intracellular glutathione (GSH) levels (Murphy T. H., et al. *Neuron* 2, 1547-1558, 1989), activation of neuronal 12-lipoxygenase (Li, Y. et al., see supra), increased ROS production (Tan S. et al., see supra) and elevated intracellular $Ca^{2+}$ (Li, Y. et al., see supra). Some molecules were measured for their ability to protect such cells against glutamate-induced stress and the assay is detailed in Example 4.

Primary embryonic hippocampal neuronal cells are widely recognized as useful in models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, *Culturing Nerve Cells,* $2^{nd}$ edition, 1998. The MIT Press, Cambridge, Mass.). The hippocampus also exhibits a remarkable capacity for activity-dependent changes in synaptic function, such as long-term potentiation (Hawkins R D, Kandel E R, Siegelbaum S A. Learning to modulate transmitter release: themes and variations in synaptic plasticity [review], *Ann. Rev Neurosci.* 16, 625-665, 1993.).

Primary cultures of hippocampal neurons measuring the ability to protect energetically competent cells were used to test compounds for activity in neuronal protection. Some molecules were measured for their ability to protect cells against one or more standard stressors, including hypoxia and the assay is detailed in Example 3.

For the purpose of the present invention other well known in the art in vitro cell-based assays such as inflammation assays, for example e-selectin (also named Endothelial Leukocyte Adhesion Molecule or ELAM) or C-reactive protein (CRP), or myocyte calcium-contractility assay or in vivo assays such as the rat middle cerebral artery occlusion (MCAO) model of cerebral ischemia assay, the rat paw edema assay or the mouse ear inflammation response to topical arachidonic acid assay or a skin protection assay may also be used. Persons well skilled in the art will readily be able to determine what assays to use to establish activity of a compound targeting a defined disorder. The above stated assays should not be considered as limiting the scope of the invention, but merely as being illustrative and representative thereof.

The present invention also relates to compositions for treating a condition characterized by oxidative stress, wherein such compositions comprise a redox-active molecule characterized by an oxidation potential, an oxidative reversibility, a reduction potential and the ability to protect energetically competent cells as described herein, said molecules being identified by the method of the present invention. Diseases, disorders, or syndromes associated with oxidative stress include, but are not limited to reperfusion injury following ischemia, myocarditis, cardiomyopathy, acute endocarditis, pericarditis, congestive heart failure, inflammatory complications of diabetes mellitus, amyetrophic lateral sclerosis, neurodegenerative diseases, such as Alzheimer's disease and dementia, autoimmune disease, Sjogren's syndrome, retinal oxidative damage, retinopathy, Crohn's disease, ulcerative colitis, angiogenesis, disorders of the peritoneal, pelvic and pleural cavity, adult respiratory distress syndrome (ARDS), lung disorders, bronchial hyperreactivity, chronic obstructive pulmonary disease (COPD), and inflammatory conditions as described herein.

As used herein, "inflammation" or "inflammation conditions" includes but is not limited to muscle fatigue, autoimmune diseases such as systemic lupus erythematosus, rheumatoid arthritis, osteoarthritis, inflammatory bowel disease, autoimmune diabetes, skin inflammation, such as atopic dermatitis, contact dermatitis, allergic dermatitis, xerosis, eczema, rosacea, seborrhea, psoriasis, thermal and radiation burns, acne, oily skin, wrinkles, excessive cellulite, excessive pore size, intrinsic skin aging, photo aging, photo damage, harmful UV damage, keratinization abnormalities, alopecia, dyspigmentation, inflammation due to wounds, scarring or stretch marks, loss of elasticity, skin atrophy and gingivitis.

As used herein, "ischemia" includes but is not limited to central nervous system ischemia resulting from cardiac arrest, hypoxemia, transient ischemic attack, stroke or severe hypotension; cerebral ischemia including stroke which may result in some degree of brain damage; ischemic heart disease (myocardial ischemia); spinal cord ischemia and paraplegia; retinal ischemia including age-related macular degeneration (ARMD); hepatic ischemia; renal ischemia; dermal ischemia; penile ischemia; pulmonary ischemia; gastric ischemia; intestinal ischemia; splenic ischemia; pancreatic ischemia; skeletal muscle ischemia; and ischemia associated with diabetic ulcers, gangrenous conditions, post-trauma syndrome, benign prostatic hyperplasia of hypertrophy (BPH), post prostate cancer surgery, cardiac arrest resuscitation, peripheral nerve damage or neuropathies.

As used herein the terms "neurodegenerative diseases or disorders, or neurodegeneration" refer to diseases or disorders characterized by a loss of neurons and may or may not include an inflammatory process. Neurodegenerative diseases or disorders include stroke, head trauma, cerebral hypoxia, spinal cord injury, epilepsy, senile dementia, Alzheimer's disease, amyotrophic lateral sclerosis (ALS), cerebral amyloid angiopathy, HIV-related dementia, Parkinson's disease, Friedreich's ataxia or other degenerative ataxias, amyloidoses, Leber's hereditary optic neuropathy (LHON), Huntington's disease, prion diseases, myasthenia gravis, Down's syndrome, prion diseases including Creutzfeldt-Jakob disease, Tay-Sach's disease, diabetic neuropathy, neuropathic pain, encephalitis, meningitis, and Duchenne's muscular dystrophy.

As used herein, "physical-chemical profile" includes but is not limited to redox profile comprising one or more parameters selected from onset of oxidation, potential of oxidation or reduction waves, reversibility of said oxidation or reduction waves, and current of said oxidation or reduction waves, optionally in conjunction with energy profile and/or transport profile, as defined herein.

As used herein, "onset of oxidation" means the potential at which the current is 1% of the maximum current.

As used herein, "profile" includes one or more parameters or measurements.

As used herein "redox parameter" or "redox property" or "redox" means a quantity related to a redox process that can be measured, e.g. potential, current, reversibility.

As used herein, "reversibility" means the measure of the reaction kinetics. It may be monitored by one or more of the following parameters, ratio of the peak currents at the anodic peak and cathodic peaks, half-width of the peaks, and/or separation of the peaks. The "reversibility of oxidation wave" as described herein, is measured by the ratio of current peak of the oxidation wave to the corresponding current peak of the reduction wave, or, in the case of more than one wave, by the ratio of the mathematical addition of the current peaks of reduction waves over the mathematical addition of the current peaks of reoxidation waves.

As used herein, "therapeutically effective amount" means an amount of a compound or composition effective to reduce or alleviate the symptoms of interest.

As used herein, "treatment" or "treating" means any treatment of a syndrome, disease or disorder in a mammal, including: preventing or protecting against the syndrome, disease or disorder, that is causing the clinical symptoms of the disease to develop; inhibiting the disease, that is, arresting or suppressing the development of clinical symptoms; and/or relieving the disease, that is, causing the regression of clinical symptoms.

As used herein a "flavonoid core structure" is a scaffold of the following structure:

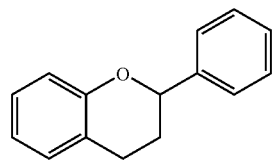

Some examples within this group are quercetin, luteolin, hesperetin, 8-acetyl quercetin, 6,8-dibromo-quercetin, anthocyanidin, and 8-(2-hydroxy)-ethyl quercetin.

As used herein a "quinone core" is a scaffold including a cyclohexadiene-dione moiety. The term "quinone core" includes but is not limited to the o-quinone scaffold, the p-quinone scaffold, the naphthoquinone scaffold and the anthraquinone scaffold.

As used herein a "stilbene core" is a scaffold of the following structure:

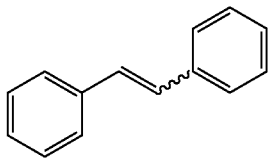

The term "stilbene core" includes cis and trans (or Z and E) single isomers, as well as a mixture of isomers.

As used herein, "disorder" means any disease, condition, symptom, or indication.

The pharmaceutical compositions utilized in this invention may be administered by any number of routes including but not limited to, oral, intravenous, intramuscular, intra-arterial, intramedullary, intrathecal, intraventricular, transdermal, subcutaneous, intraperitoneal, intranasal, enteral, topical, sublingual or rectal means. In addition to the active ingredients, these pharmaceutical compositions may contain suitable therapeutically-acceptable carriers comprising excipients and auxiliaries which facilitate processing of the active compounds into preparations which can be used pharmaceutically, therapeutically, or neutraceutically. Further detail on technique for formulation and administration may be found in the latest edition of Remington's Pharmaceutical Sciences (Mack Publishing Co., Easton, Pa.) hereby incorporated by reference in its entirety.

Pharmaceutical compositions suitable for use in the invention include compositions wherein the active ingredients are contained in an effective amount to achieve the intended purpose. The determination of an effective dose is well within the capability of those skilled in the art. For any compound, the therapeutically effective dose can be estimated initially either in cell culture assays, e.g. neuronal cells, or in animal models, usually mice or rats. The animal model may also be used to determine the appropriate concentration range and route of administration. Such information can then be used to determine useful doses and routes of administration.

The exact dosage will be determined by the practitioner in light of factors related to the subject that requires treatment. Dosage and administration are adjusted to provide sufficient levels of the active moiety or to maintain the desired effect. Factors which may be taken into account include the severity of the disease state, general health or the subject, age, weight, and gender of the subject, diet, time and frequency of administration, drug combination(s), reaction sensitivities, and tolerance/response to therapy.

Administration of the compositions of the invention can be via any of the accepted modes of administration for agents that serve similar utilities.

While human dosage levels have yet to be optimized for the compounds of the invention, generally, a daily dose is from about 0.01 to 15.0 mg/kg of body weight, preferably about 0.1 to 7.5 mg/kg of body weight, and most preferably about 0.3 to 1.5 mg/kg of body weight. Thus, for administration to a 70 kg person, the dosage range would be about 0.7 to 1,000 mg per day, preferably about 7.0 to 500 mg per day, and most preferably about 21 to 100 mg per day. The amount of active compound administered will, of course, be dependent on the subject and disease state being treated, the severity of the affliction, the manner and schedule of administration and the judgment of the prescribing physician.

Compositions of the invention may be employed in any skin care application where decreased inflammatory response is desirable. For example, compositions of the invention may be incorporated into leave-on and rinse-off acne preparations, facial milks and conditioners, shower gels, foaming and non-foaming facial cleansers, cosmetics, hand and body lotions, leave-on moisturizers, cosmetic and cleaning wipes, salves for poison ivy, chicken pox, pruritus, or the like. Generally, for dermal applications, topical administration is preferred; however, systemic administration, as described elsewhere herein, is also possible.

In employing the compositions of this invention for treatment of the above conditions, any therapeutically acceptable mode of administration can be used. The redox active molecules can be administered either alone or in combination with other therapeutically acceptable excipients, including solid, semi-solid, liquid or aerosol dosage forms, such as, for example, tablets, capsules, powders, liquids, suspensions, suppositories, aerosols or the like. The compositions can also be administered in sustained or controlled release dosage forms, including depot injections, osmotic pumps, pills, transdermal (including electro-transport) patches, and the like, for the prolonged administration of the compound at a predetermined rate, preferably in unit dosage forms suitable for single administration of precise dosages. The compositions will typically include a conventional pharmaceutical carrier or excipient, and a redox-active molecule. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the therapeutically acceptable composition will contain about 0.1% to 90%, preferably about 0.5% to 50%, by weight of a redox-active molecule, the remainder being suitable pharmaceutical excipients, carriers, etc.

One preferred manner of administration for the conditions detailed above is oral, using a convenient daily dosage regimen which can be adjusted according to the degree of affliction. For such oral administration, a therapeutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid therapeutically administrable compositions can, for example, be prepared by dissolving, dispersing, etc. a redox-active compound and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa. 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a therapeutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410, 545. For a liquid dosage form, the solution, e.g. in a polyethylene glycol, may be diluted with a sufficient quantity of a therapeutically acceptable liquid carrier, e.g. water, to be easily measured for administration.

Alternatively, liquid or semi-solid oral formulations may be prepared by dissolving or dispersing the redox-active compound in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. No. Re. 28,819 and U.S. Pat. No. 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution. Nasal solutions of the active compound alone or in combination with other therapeutically acceptable excipients can also be administered.

EXAMPLES

Example 1

Cyclic Voltammetry Measurement

The cyclic voltammetry measurement was conducted in a three-electrode system comprising a microelectrode made from platinum (a disk of 1.6 $mm^2$ area), a counter electrode made from a coiled platinum wire and a silver/silver chloride reference electrode, on a voltammetric analyzer Epsilon with a C-3 cell, all from Bioanalytical Systems (West Lafayette, Ind.).

a. Preparation of the Solution

A solution of tetrabutyl ammonium perchlorate (TBAP) (500 mM final concentration) in N,N-dimethyl formamide (DMF) (5 mL) was prepared in a graduated flask. The compound was added to reach a concentration of 10 mM. The solution was stirred and sonicated if necessary to make sure that the compound was fully dissolved.

b. Preparation of the Electrodes

The reference electrode was kept in a 3 M solution of NaCl in distilled water. The reference electrode was rinsed with water, then methanol, and dried by air blow. The reference electrode was gently shaken, if necessary, to remove any air bubble within the base.

The auxiliary electrode was rinsed with water, then methanol and dried by air blow.

The working electrode was polished on a nylon pad coated with a 1 µ-meter diamond slurry in oil, then rinsed thoroughly with methanol. It is then polished on a corduroy pad coated with a 0.15 µ-meter alumina slurry in water, then rinsed thoroughly with water and methanol, then dried by air blow.

Prior to beginning a measurement and when changing compound solutions, the electrochemical cell was thoroughly cleaned with methanol, including glass reservoir, Teflon cap, and purge lines. Likewise, all electrodes were cleaned with methanol upon removal for any reason, including prior to polishing the working electrode between runs. While the working electrode was being polished, the reference electrode was removed from the test solution, rinsed with methanol and water, and stored in aqueous 3M NaCl solution.

c. Method Parameters

| Reduction | Oxidation |
|---|---|
| Initial potential: 0 mV | Initial potential: 0 mV |
| Switching potential #1: −1800 mV | Switching potential #1: 1800 mV |
| Switching potential #2: 1800 mV | Switching potential #2: −1800 mV |
| Final potential: −800 | Final potential: 800 |
| Number of segments: 3 | Number of segments: 3 |
| Scan rate: 100 mV/s, 2000 mV/s, 20 mV/s | Scan rate: 100 mV/s, 2000 mV/s, 20 mV/s |

Other parameters could be investigated after the initial oxidative and reductive runs. The parameters of such runs are highly compound dependent and it is up to the judgment of those collecting data, but minimally the above parameters should be used.

d. Assembling of Cell and Purge

The solution containing the compound was transferred into the cell, where the three electrodes were immersed. The solution was stirred and purged with dry argon for at least 1 minute to remove any oxygen, after which a blanket of argon was kept above the solution to prevent any diffusion of oxygen. Stirring was halted prior to collecting data. Care was taken to ensure there were no bubbles attached to any of the electrodes prior to beginning electrochemical measurements.

e. Run iR Compensation

The solution is not a perfect conductor, and its resistance R introduces a voltage drop when a current flows between the working to the auxiliary electrode. This voltage drop introduces an error between the nominal voltage imposed by the voltammetric analyzer and the actual voltage between the working and auxiliary electrodes. The instrument can automatically measure and compensate for this iR drop, using the "iR Compensation" feature of the software. Normal values are the following:
Cell resistance R<1000 ohms
RC constant>10 μs
% resistance to be compensated: 50 to 100%
Uncompensated resistance<(R−300 ohms)

f. Run

The cyclic voltammogram was recorded. After each cyclic voltammogram was recorded, the working electrode was polished again, as indicated above, to regenerate a clean, electroactive surface.

Example 2

Square Wave Voltammetry Measurement

The square wave voltammetry measurement was conducted in a three-electrode system comprising a microelectrode made from platinum (a disk of 1.6 mm² area), a counter electrode made from coiled platinum wire and a silver/silver chloride reference electrode, on a voltammetric analyzer CV-50W with a C-3 cell, all from Bioanalytical Systems (West Lafayette, Ind.).

Procedure a. Prepare the Solution

A solution of tetrabutyl ammonium perchlorate (TBAP) (500 mM final concentration) in N,N-dimethyl formamide (DMF) (5 mL) is prepared in a graduated flask. The compound is added to reach an arbitrary concentration, 10 mM is desired but less is acceptable. This method is especially useful for low concentration analytes, those molecules that are difficult to dissolve in DMF or available only in small quantities. The solution is stirred and sonicated if necessary to make sure that the compound is dissolved to the best of its ability.

b. Prepare the Electrodes

The reference electrode is kept in a 3 M solution of NaCl in distilled water. The reference electrode is rinsed with water, then methanol, and dried by air blow. The reference electrode is gently shaken, if necessary, to remove any air bubble at the base.

The auxiliary electrode is rinsed with water, then methanol and dried by air blow.

The working electrode is polished on a nylon pad coated with a 1 μ-meter diamond slurry in oil, then rinsed thoroughly with methanol. It is then polished on a corduroy pad coated with a 0.15 μ-meter alumina slurry in water, then rinsed thoroughly with water and methanol, then dried by air blow.

Prior to beginning and when changing compound solutions, the electrochemical cell should be thoroughly cleaned with methanol including the glass reservoir, Teflon cap, and purge lines. Likewise, all electrodes should be promptly cleaned with methanol upon removal for any reason, including prior to polishing the working electrode between runs. While the working electrode is being polished, the reference electrode should be removed from the test solution, rinsed with methanol and water, and stored in aqueous 3M NaCl solution.

c. Enter Method Parameters

| Reduction | Oxidation |
|---|---|
| Initial potential: 1800 mV | Initial potential: −1800 mV |
| Switching potential #1: −1800 mV | Switching potential #1: 1800 mV |
| Step Potential: 4 | Step Potential: 4 |
| Amplitude: 25 | Amplitude: 25 |
| Frequency: 15 | Frequency: 15 |

The above conditions should be repeated for the following sets of step potentials, amplitudes, and frequencies (4,50,30), (2,25,15)

Other parameters could be investigated after the initial oxidative and reductive runs. The parameters of such runs are highly compound dependent and it is up to the judgment of those collecting data, but minimally the above parameters should be used.

d. Assemble Cell and Purge

The solution containing the compound is transferred into the cell, where the three electrodes are immersed. The solution is stirred and purged with dry argon for at least 1 minute to remove any oxygen, after which a blanket of argon is kept above the solution to prevent any diffusion of oxygen. Stirring is halted prior to collecting data. Care must be taken to ensure there are no bubbles attached to any of the electrodes prior to beginning electrochemical measurements.

d. Run

The voltammogram can then be recorded. After each square wave voltammogram is recorded, the working electrode is polished again, as indicated above, to regenerate a clean, electroactive surface.

Example 3

Determination of Activity Utilizing the Cell Elam Assay

Endothelial-Leukocyte Adhesion Molecule (ELAM), also known as E-selectin, is expressed on the surface of endothelial cells. In this assay, lipopolysaccharide (LPS) and IL-1β were used to stimulate the expression of ELAM; test agents were tested for their abilities to reduce this expression, in accordance with studies showing that reduction of leukocyte adhesion to endothelial cell surface was associated with decreased cellular damage (e.g., Takada, M. et al., Transplantation 64: 1520-25, 1997; Steinberg, J. B. et al., J. Heart Lung Trans. 13:306-313, 1994).

Endothelial cells may be selected from any of a number of sources and cultured according to methods known in the art; including, for example, coronary artery endothelial cells, human brain microvascular endothelial cells (HBMEC; Hess, D. C. et al., Neurosci. Lett. 213(1): 37-40, 1996), or lung endothelial cells. Cells were conveniently cultured in 96-well plates. Cells were stimulated by adding a solution to each well containing 10 µg/ml LPS and 100 pg/ml IL-1β for 6 hours in the presence of test agent (specific concentrations and time may be adjusted depending on the cell type). Treatment buffer was removed and replaced with pre-warmed Fixing Solution® (100 µL/well) for 25 minutes at room temperature. Cells were then washed 3×, then incubated with Blocking Buffer (PBS+2% FBS) for 25 minutes at room temperature. Blocking Buffer containing Monoclonal E-Selectin Antibody (1:750, Sigma Catalog #S-9555) was added to each well. Plates were sealed and stored at 4° overnight. Plates were washed 4× with 160 µL Blocking Buffer per well. Second Antibody-HRP diluted 1:5000 in Blocking Buffer was then added (100 µL/well), and plates were incubated at room temperature (protected from light) for two hours. Plates were then washed 4× with Blocking Buffer before addition of 100 µL of ABTS Substrate solution at room temperature (Zymed, Catalog #00-2024). Wells were allowed to develop for 35 minutes, before measurement at 402 nm in a Fluoroskan® Reader with shake program for 10 seconds. Positive results were recorded as a decrease in ELAM concentration in tested wells, as compared to control wells.

Example 4

Determination of Activity Utilizing Neuronal Cell Stress Assay

This assay was used to induce ischemia by anoxia-reoxygenation in cultured hippocampal neuronal cells. Test compounds were added to assess potency and efficacy against ischemia-induced neuronal cell injury and cell death.

Isolation and Culture of Primary Hippocampal Neuronal Cells.

Materials:

Neurobasal/B27i: Neurobasal medium (available from Invitrogen, San Diego, Calif.) with 1× B27 supplement (Invitrogen), 0.5 µM L-glutamine, 25 µM L-glutamic acid, and 1×Penicillin/Streptomycin.

Hank's Basic Salt Solution (HBSS, Ca/Mg-free) is prepared by preparing 1× Hanks CMF (Gibco) supplemented with HEPES (10 mM, pH 7.3), sodium bicarbonate (0.35%), 1× Penicillin/Streptomycin, and 1 mM MEM sodium pyruvate.

Poly-D-lysine (Sigma, St. Louis, Mo.), 50 µg/ml solution.
Sigmacote (Sigma, St. Louis, Mo.).
Plastic Culture Flasks (T75 cm$^2$) or 24-well cell culture plates treated with Poly-D-Lysine (Sigma, St. Louis, Mo.).

Experimental Setup:

A pregnant female mouse (E18-E19) was euthanized with $CO_2$ followed by removal of the uterus, which was then placed in a sterile plastic petri dish. The embryos were removed from the sac, and the embryonic brains removed and immersed in cold (4° C.) Buffered Salt Solution (HBSS; Ca/Mg free; Life Technologies) in a small petri dish. Hippocampi were then removed from the brains under a dissecting microscope and placed on a paraffin-covered dish. The meninges were stripped away and the dissected hippocampi were collected in a small petri dish in HBSS. The hippocampi were transferred to a 15-ml centrifuge tube (normally 10-12 brains) filled with HBSS. The tube containing the brains was centrifuged at 1000 rpm for 2 min in a tabletop centrifuge. The supernatant was removed, 2 ml of HBSS was added to the hippocampi in the tube, and the resulting suspension was triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension was then centrifuged again at 1000 rpm for 2 min in a tabletop centrifuge, the supernatant was discarded, and 2 ml of Neurobasal/B27i (with antibiotics) was added to the tube. The trituration procedure described above was then repeated on this suspension.

The density of cells was determined on a small aliquot of cells using standard counting procedures and correcting for cell viability by trypan blue stain exclusion. Using this procedure, the expected yield is $3 \times 10^5$-$6 \times 10^5$ cells/brain. Cells were then added to PDL-coated 24 well plates, flasks or MetTek dishes in Neurobasal/B27l at a density of about $1.5 \times 10^6$ cells (T75 flask) or about 100,000 cells/well of a 24-well plate. Plated cells were incubated at 37° C. in an atmosphere of 5% $CO_2$/95% $O_2$. Media was renewed after 3-4 days by replacing half of it with fresh Neurobasal/B27m medium, containing 5 µM cytosine arabinoside (Ara-C). Seven to eight days from the initial culture, the media was renewed again, by removing one-half or it and replacing with an equal amount of fresh Neurobasal/B27m medium (without Ara-C).

Hippocampal Anoxia-Reoxygenation Cell Death Assay.

Materials:

Neurobasal media, NoG neurobasal media, B27 supplement and B27 Supplement minus AO (Invitrogen).

Neurobasal/B27 medium is prepared with 2× B27 minus AO supplement, 0.5 mM L-glutamine and 0.25× penicillin/streptomycin.

Cell Tracker Green was obtained from Molecular Probes and a fresh 5 µM solution was prepared from 10 mM stock just before use.

NoG-Neurobasal contains NoG neurobasal medium plus 0.5 mM glucose, 0.1 mM L-glutamine and 0.25× Penicillin/Streptomycin.

Experimental Setup:

Primary hippocampal neuronal cells were prepared according to the methods described above and were cultured in poly-D-lysine coated 24 well plates for 10-11 days prior to use.

Deoxygenated LoG-Neurobasal medium (100 ml) was prepared by pre-equilibrating the medium in a T150 cm$^2$ flask in a hypoxic chamber overnight. Following pre-incubation under hypoxic conditions, the LoG-Neurobasal media was lightly bubbled with 100% $N_2$ for 30 min to completely deoxygenate the media. An additional 20 ml LoG-Neurobasal was pre-equilibrated in a T75 cm$^2$ flask and 100 ml Neurobasal/B27AO was incubated in a normal incubator (5% $CO_2$) overnight. Reoxygenated medium was prepared by placing medium overnight in the culture incubator (5% $CO_2$/95% $O_2$) prior to use.

Existing culture medium (Neurobasal/B27m) was removed from the cells by aspiration. Cells were washed once with 2 ml/well (24-well culture plates) of glucose free-BSS. Neurons were replenished 10-11 days after initial culture with deoxygenated LoG-Neurobasal (11 ml per well for each well of a 24-well plate). Test compounds were added directly to each well (3 concentrations of the compound plus positive control, each in triplicate). Most test compounds were dissolved in 100% DMSO; concentrations were adjusted such that the final concentration of DMSO in the cell media never exceeded 0.5%. Plates containing cells with test compounds were placed in a hypoxic chamber for 5 hr with plate lids ajar.

For normoxia controls, pre-equilibrated normoxic LoG-Neurobasal medium was added to each well of cells, and the plate was replaced in the normal culture incubator for 5 hr. After 5 hr of hypoxia, the existing media was carefully aspirated off, and 2 mL of new, re-oxygenated (pre-equilibrated) Neurobasal/B27AO was added to each well. The same test compounds (in the same the concentrations) were added back into the corresponding wells. Plates were placed in the cell culture incubator (5% $CO_2$/95% $O_2$) and re-oxygenated for 20-24 hr. After reoxygenation for 20-24 hr, live neurons were quantitated using the cell tracker green fluorescence method, described below.

To test for cell viability, existing culture medium was aspirated from each well of the 24 well plates, and neurons were washed once with 2 ml of HBSS (pH 7.4, pre-warmed to 30-37° C.). To each well was added one milliliter of 5 μM Cell Tracker Green fluorescent dye dissolved in HBSS. Plates were placed in the dark at room temperature for 15 minutes, and are then washed with two milliliters of HBSS. One milliliter of HBSS was then added to each well, and fluorescent cells were counted using a fluorescent microscope. Significantly increased cell viability compared to control cells was indicative of a protective compound.

Example 5

High Glutamate-Induced Oxidative Stress Assay (HGOS)

This procedure was used to induce high glutamate-induced oxidative stress (HGOS) in a dopaminergic neuronal cell line. Using this assay the potency and efficacy of test articles against HGOS neuronal cell injury and cell death can be established in a high throughput manner.

Materials
   Dopaminergic neuronal cell lines
   DMEM-No Glucose (Life Technologies Cat #11966-025)
   L-glutamine (Life Technologies Cat #25030-081)
   L-glutamic acid, monosodium salt (Sigma Cat #G5889)
   D-glucose (Sigma Cat #G-6151)
   10× HBSS buffer(pH 7.4) (950 ml Pyrogen-free water, 2.44 g/L MgCl2.6 H20, 3.73 g/L KCl, 59.58 g/L Hepes, 58.44 g/L NaCl, 1.36 g/L KH2PO4, 1.91 g/L CaCl2.2H2O and pH to 4.5 with HCl)
   Cell Tracker Green fluorescent dye (Molecular Probes, Cat #2925). Prepare a 5 μM solution in pre-warmed HBSS just prior to use.
   Sterile 96-well plates precoated with poly-D-lysine (Corning Catalog #3665)
   96-well deep well mother plate, DyNA Block 1000 (VWR Catalog #40002-008)

Neuronal Cells
The cells were seeded into 96-well plates at a density of 2000 per well and left to grow for 72 hours in a 33° C. incubator with 5% $CO_2$ in air atmosphere. The passage number of the cells for each assay experiment were no later than p11 in order to minimize experimental variation.

Compound Preparation in Deep-well Mother Plates
   VWRBrand DyNA Block 1000, deep well mother plates (VWR Cat. #40002-008) were used for the preparation of the test compounds.
   All compounds were dissolved in DMEM-No Glu containing 1 mM glucose, 30 mM glutamate and 1× Pen/Strep. DMEM-No Glu with 1 mM glucose and 1× P/S was used as the negative control, DMEM-No Glucose with 1 mM glucose, 100 M glutamate was used as a positive control and 100 μM Glutathione was added to the positive control as a standard. All of the procedures for this involving the making and dilution of compounds were performed using aseptic conditions and with minimal light.

Cell Preparation
The plates were removed from the incubator and examined under the microscope for morphological appearance and density. Using an aseptic technique and an 8-channel aspirator the media was carefully removed from the cells and replaced with 200 μL of 1× HBSS. This was done as quickly as possible to prevent the cells drying out. The plates were then placed in the humidified 37° C. incubators of the Biomek 2000 Side Loader. Four plates were washed at a time so as to minimize the time that the cells were sitting in 1× HBSS prior to addition of the compound test solution.

Experimental Setup
The Beckman Biomek workstations were used to load the compounds and controls from the mother plates onto the cell plates that were prewashed with HBSS under sterile conditions. The plates were incubated in the upper HTS incubator at 37° C. in 5% $CO_2$ for exactly 16 hrs. The following day, using the Beckman Biomek workstations, the plates were removed from the incubator. Using Cell Tracker Addition, the compounds were removed from the plates, washed once with 200 μM of pre-warmed 1× HBSS and then 100 μL of 5 μM Cell Tracker Green was added to each well. The plates were incubated at 37° C. for 30 min to allow the dye to enter the cell and be cleaved by the esterases. After washing the cells twice with prewarmed 1× HBSS, the plates were read with the 485 excitation; 538 emission filter pair on a Fluoroskan.

What is claimed is:

1. A method of identifying and selecting therapeutic compounds having a predetermined core structure, said method comprising:
   establishing a relationship between physical-chemical profile and biological activity; wherein the physical-chemical profile comprises one or more parameters selected from reversibility of one or more oxidation waves or reversibility of one or more reduction waves; and wherein the biological activity is measured in an assay effective in detecting compounds for the treatment of a targeted disorder;
   testing further potential therapeutic candidates with said core structure for their physical-chemical properties; and
   selecting therapeutic compounds based on their physical-chemical parameters falling within a range predefined by the physical-chemical/biological relationship of the previously tested subset of compounds.

2. The method of claim 1, wherein the physical-chemical profile comprises the parameter for reversibility of one or more oxidation waves.

3. The method of claim 1, wherein the physical-chemical profile comprises the parameter for reversibility of one or more reduction waves.

4. The method of claim 3, wherein the biological activity assay comprises the E-selectin (ELAM) cell based assay detecting compounds with an $EC_{50}$ lower than 30 μM versus a silver/silver chloride reference electrode.

5. The method of claim 4, wherein the therapeutic compound is selected if it comprises a quinone core structure and if its physical-chemical profile comprises a parameter for the total reversibility of reduction of 75% or more.

6. The method of claim 5, wherein the physical-chemical profile additionally comprises one or more parameters selected from the energy profile parameters and the transport profile parameters.

7. The method of claim 5 wherein the compound is for the treatment of a condition characterized by oxidative stress.

8. The method of claim 1, wherein the assay is a cell-based assay comprising one or more assays selected from the High Glutamate-Induced Oxidative Stress (HGOS) assay wherein the compounds in the previously tested subset group of compounds have the ability to protect at least 30% of energetically competent cells against stressor induced cell death; and the E-selectin (ELAM) assay wherein the compounds in the previously tested subset group of compounds exhibit an $EC_{50}$ lower than about 30 μM.

9. The method of claim 8, wherein the therapeutic compound is selected if it comprises a stilbene core structure and if its physical-chemical profile comprises one or more parameters selected from the parameter for potential of the first oxidation wave that falls between about 800 mV and 1400 mV versus a silver/silver chloride reference electrode, and the parameter for the reversibility of the first oxidation wave that measures about 20% or more.

10. The method of claim 9, wherein the physical-chemical profile additionally comprises one or more parameters selected from the energy profile parameters and the transport profile parameters.

11. The method of claim 9, wherein the therapeutic compound is for the treatment of a condition characterized by oxidative stress.

12. The method of claim 8, wherein the therapeutic compound is selected if it comprises a core structure of Formula I:

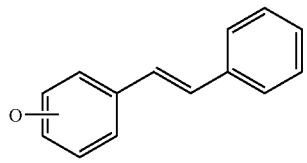

Formula I wherein additional substitution at the phenyl rings does not include a nitro group; and if its physical-chemical profile comprises the parameter for potential of the first oxidation wave that falls below 1000 mV versus a silver/silver chloride reference electrode.

13. The method of claim 12, wherein the physical-chemical profile additionally comprises one or more parameters selected from the energy profile parameters and the transport profile parameters.

14. The method of claim 12, wherein the therapeutic compound is for the treatment of a condition characterized by oxidative stress.

15. The method of claim 8, wherein the therapeutic compound is selected if it comprises a core structure of Formula I:

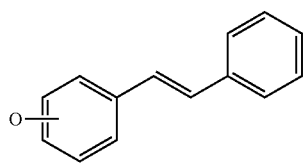

Formula I wherein additional substitution at the phenyl rings includes a nitro group; and if its physical-chemical profile comprises one or more parameters selected from the parameter for potential of the first oxidation wave that falls between about 950 mV and 1250 mV versus a silver/silver chloride reference electrode, and the parameter for reversibility of the first oxidation wave measures more than 20%.

16. The method of claim 15, wherein the physical-chemical profile additionally comprises one or more parameters selected from the energy profile parameters and the transport profile parameters.

17. The method of claim 15, wherein the therapeutic compound is for the treatment of a condition characterized by oxidative stress.

18. A method of identifying and selecting therapeutic compounds having a predetermined core structure, said method comprising:

establishing a relationship between physical-chemical profile and biological activity; wherein the physical-chemical profile comprises a parameter for onset of oxidation; and wherein the biological activity is measured in an assay comprising the E-selectin (ELAM) cell based assay detecting compounds with an $EC_{50}$ lower than 30 μM;

testing further potential therapeutic candidates with said core structure for their physical-chemical properties; and selecting therapeutic compounds based on their physical-chemical parameters falling within a range predefined by the physical-chemical/biological relationship of the previously tested subset of compounds.

19. The method of claim 18, wherein the therapeutic compound is selected if it comprises a flavonoid core structure of Formula II:

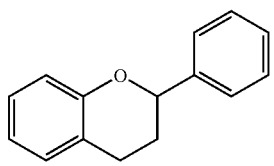

Formula II wherein none of the substituents are hydroxy groups;

and if its physical-chemical profile comprises the parameter for onset of oxidation that falls between about 850 mV and 1050 mV versus a silver/silver chloride reference electrode.

20. The method of claim 19, wherein the physical-chemical profile additionally comprises one or more parameters selected from the energy profile parameters and the transport profile parameters.

21. The method of claim 19, wherein the therapeutic compound is for the treatment of a condition characterized by inflammation.

22. The method of claim 18, wherein the therapeutic compound is selected if it comprises a flavonoid core structure of Formula II:

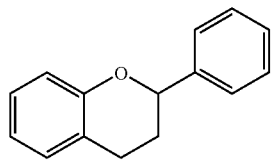

Formula II wherein one or more of the substituents are hydroxy groups;
and if its physical-chemical profile comprises the parameter for onset of oxidation that falls between about 350 mV and 650 mV versus a silver/silver chloride reference electrode.

23. The method of claim 22, wherein the physical-chemical profile additionally comprises one or more parameters selected from the energy profile parameters and the transport profile parameters.

24. The method of claim 22, wherein the therapeutic compound is for the treatment of a condition characterized by inflammation.

25. A method of identifying and selecting therapeutic compounds having a predetermined core structure, said method comprising:
establishing a relationship between physical-chemical profile and biological activity; wherein the physical-chemical profile comprises a parameter for potential of oxidation wave; and wherein the biological activity is measured in an assay comprising an HGOS assay protecting at least 30% of the cells against stressor induced cell death;
testing further potential therapeutic candidates with said core structure for their physical-chemical properties; and
selecting therapeutic compounds based on their physical-chemical parameters falling within a range predefined by the physical-chemical/biological relationship of the previously tested subset of compounds.

26. The method of claim 25, wherein the therapeutic compound is selected if it comprises a flavonoid core structure and if its physical-chemical profile comprises the parameter for oxidation potential that falls between about 1050 mV and 1450 mV versus a silver/silver chloride reference electrode.

27. The method of claim 26, wherein the physical-chemical profile additionally comprises one or more parameters selected from the energy profile parameters and the transport profile parameters.

28. The method of claim 26, wherein the therapeutic compound is for the treatment of a condition characterized by oxidative stress.

29. The method of claim 25, wherein the therapeutic compound is selected if it comprises a chroman core structure of Formula IV,

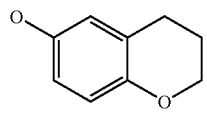

Formula IV and if its physical-chemical profile comprises the parameter for oxidation potential that falls between about 850 mV and 1200 mV versus a silver/silver chloride reference electrode.

30. The method of claim 29, wherein the physical-chemical profile additionally comprises one or more parameters selected from the energy profile parameters and the transport profile parameters.

* * * * *